US007592507B2

(12) United States Patent
Beeckman et al.

(10) Patent No.: US 7,592,507 B2
(45) Date of Patent: Sep. 22, 2009

(54) METHOD TO MODIFY CELL NUMBER, ARCHITECTURE AND YIELD OF PLANTS BY OVEREXPRESSING THE E2F TRANSCRIPTION FACTOR

(75) Inventors: Tom Beeckman, Merelbeke (BE); Lieven De Veylder, Drongen (BE); Dirk Inze, Moorsel-Aalst (BE); Vladimir Mironov, Ghent (BE); Willem Broekaert, Dilbeck (BE); Willy Dillen, St-Amandsberg (BE); Valerie Frankard, Brussels (BE)

(73) Assignee: CrooDesign, N.V., Ghent (BE)

( * ) Notice: Subject to any disclaimer, the term of this patent is extended or adjusted under 35 U.S.C. 154(b) by 171 days.

(21) Appl. No.: 10/489,500

(22) PCT Filed: Sep. 12, 2002

(86) PCT No.: PCT/EP02/10236

§ 371 (c)(1),
(2), (4) Date: Sep. 30, 2004

(87) PCT Pub. No.: WO03/025185

PCT Pub. Date: Mar. 27, 2003

(65) Prior Publication Data

US 2005/0059154 A1 Mar. 17, 2005

(30) Foreign Application Priority Data

Sep. 14, 2001 (EP) ................................ 01870198

(51) Int. Cl.
*C12N 15/82* (2006.01)

(52) U.S. Cl. ........................ 800/290; 435/468; 435/430

(58) Field of Classification Search ....................... None
See application file for complete search history.

(56) References Cited

FOREIGN PATENT DOCUMENTS

| | | |
|---|---|---|
| EP | WO 99/58681 | * 11/1999 |
| WO | WO 99/58681 | 11/1999 |
| WO | WO 01/21644 | 3/2001 |

OTHER PUBLICATIONS

Ramirez-Parra E. et al. The cloning of plant E2F, a retinoblastoma-binding protein, reveals unique and conserved features with animal G(1)/S regulators. Nucleic Acids Res. Sep. 1, 1999;27(17):3527-33.*

Trieu A.T. et al. Transformation of *Medicago truncatula* via infiltration of seedings or flowering plants with Agrobacterium. Plant J. Jun. 2000;22(6):531-41.*

Ramirez-Parra E. et al. The cloning of plant E2F, a retinoblastoma-binding protein, reveals unique and conserved features with animal G(1)/S regulators, Nucleic Acids Res. Sep. 1, 1999;27(17):3527-33.*

Sawado T et al. dE2F2, a novel E2F-family transcription factor in *Drosophila melanogaster*. Biochem Biophys Res Commun. Oct. 20, 1998;251(2):409-15.*

Sekine M. et al. Isolation and characterization of the E2F-like gene in plants. FEBS Lett. Oct. 22, 1999;460(1):117-22.*

Albani D. et al. DcE2F, a functional plant E2F-like transcriptional activator from *Daucus carota.* J Biol Chem. Jun. 23, 2000;275(25):19258-67.*

Mariconti L. et al. The E2F family of transcription factors from *Arabidopsis thatliana.* Novel and conserved components of the retinoblastoma/E2F pathway in plants. J Biol Chem. Mar. 22, 2002;277(12):9911-9. Epub Jan. 10, 2002.*

Albani, D. et al. (2000) "DcE2F, a Functional Plant E3F-like Transcriptional Activator from *Daucus carota" The Journal of Biological Chemistry*, 275(25):19258-19267.

Bergounioux, C. (2001) "*Arabidopsis thaliana* mRNA for E2F protein", *EMBL* AJ276619.

De Veylder, Lieven, et al. (2002) "Control of Proliferation, endoreduplication and differentiation by the *Arabidopsis* E2Fa-DPa transcription facotr", *The EMBO Journal*, 21(6):1360-1368.

Grafi, G., et al. (1995) "E2F- and E1A-associated kinase are involved in regulating endoreduplication during maize endosperm development", *Journal of Cellular Biochemistry*, 21A:450.

Ramierz-Parra, E., et al. (2000) "Characterization of wheat DP, a heterodimerization partner of the plant E2F transcription factor which stimulates E2F-DNA binding" *FEBS Letters* 486:73-78.

Ramierz-Parra, E., et al. (1999) "The cloning of plant E2F, a retinoblastomer-binding protein, reveals unique and conserved features with animal G(1)/S regulators", *Nucleic Acids Research*, 27(17):3527-3533.

Yang, Hai Liang, et al. (1999) "Adenovirus-mediated E2F-1 Gene Transfer Inhibits MDM2 Expression and Efficiently Induces Apoptosis in MDM-2 overexpressing Tumor Cells" *Clinical Cancer Research*, 5:2242-2250.

* cited by examiner

*Primary Examiner*—Cynthia Collins
(74) *Attorney, Agent, or Firm*—Ann R. Pokalsky; Dilworth & Barrese, LLP

(57) ABSTRACT

The present invention relates to a method for modifying plant growth and development processes by affecting cell cycle regulation comprising modulating expression of members of the plant E2F transcription factor family. More specific the invention relates to methods for stimulating cell division in a plant. The invention further relates to transgenic plants produced by the methods of the invention having altered plant growth and development characteristics compared to their isogenic counterparts. Preferably, the plant characteristics modified by the present invention include enlarged cotyledons, enhanced growth rate, stress resistance and seedling survival, more cells, more tillers, more panicles.

5 Claims, 15 Drawing Sheets

Nucleotide sequence (SEQ ID NO 1) and amino acid sequence (SEQ ID NO 2) of the Arabidopsis E2F transcription factor.

SEQ ID NO 1

```
atgtccggtg tcgtacgatc ttctcccggt tcttctcagc cgccaccgcc gccgccgcac
catccaccgt catctccggt tccggttaca tctacgccgg ttataccacc tatacgtcgt
cacttagctt tcgcctcaac aaaacctccg tttcatcctt ccgatgatta ccatcgattt
aacccttctt cgctcagtaa taataacgac aggagcttcg ttcatggttg tggtgttgta
gatcgggagg aagatgctgt cgttgttaga tctccttcac gaaagagaaa ggcgacaatg
gatatggttg ttgctccatc taataatgga ttcacgagtt ctggtttcac taacatacct
agcagtccct gtcaaactcc tagaaaaggg ggcagagtca acatcaagtc aaaggccaaa
ggaaacaagt caactcctca aacacccatc tcgacaaacg ctggttctcc tatcacactt
actccatcag gaagttgtcg ttatgacagt tctttaggtc tccttacaaa aaagttcgtc
aatctaatta aacaagccaa agatggaatg ctggacctaa acaaagctgc agaaacattg
gaggtgcaga aacgacgtat atatgatatt acaaacgttt tggaggggat agatctcatt
gaaaagcctt tcaagaatcg aatactttgg aagggagttg atgcgtgtcc tggcgatgag
gatgctgacg tatctgtatt acagctgcag gcagaaattg aaaacctcgc cctcgaagag
caagcattag acaaccaaat cagacaaaca gaggaaagat taagagacct gagcgaaaat
gaaaagaatc agaaatggct tttgtaact gaagaggata tcaagagttt accaggtttc
cagaaccaga ctctgatagc cgtcaaagct cctcatggca caactttgga agtgcctgat
ccagatgaag cggctgacca cccacaaagg agatacagga tcattcttag aagtacaatg
ggacctattg acgtatacct cgtcagcgaa tttgaaggga aattcgaaga cacaaatggg
agtggtgcag caccaccagc atgcttgcct attgcttcta gctcaggatc tacaggacac
catgacatcg aagccttaac tgttgacaac ccagaaactg ctattgtgtc tcatgatcat
cctcatcctc aacccggcga tacctctgat cttaattatt tgcaagagca agtaggagga
atgcttaaga ttactccctc tgatgttgaa aatgatgagt cggactactg gcttctctca
aatgctgaga ttagcatgac ggatatttgg aaaactgact ctggtatcga ttgggattat
ggaatagccg acgtgagtac tccaccacca ggaatgggcg aaatagcacc aacagctgtt
gactcaaccc cgagatga
```

SEQ ID NO 2

```
MSGVVRSSPGSSQPPPPPPHHPPSSPVPVTSTPVIPPIRRHLAFASTKPPFHPSDDYHRFNPSSLS
NNNDRSFVHGCGVVDREEDAVVVRSPSRKRKATMDMVVAPSNNGFTSSGFTNIPSSPCQTPRKGGR
VNIKSKAKGNKSTPQTPISTNAGSPITLTPSGSCRYDSSLGLLTKKFVNLIKQAKDGMLDLNKAAE
TLEVQKRRIYDITNVLEGIDLIEKPFKNRILWKGVDACPGDEDADVSVLQLQAEIENLALEEQALD
NQIRQTEERLRDLSENEKNQKWLFVTEEDIKSLPGFQNQTLIAVKAPHGTTLEVPDPDEAADHPQR
RYRIILRSTMGPIDVYLVSEFEGKFEDTNGSGAAPPACLPIASSSGSTGHHDIEALTVDNPETAIV
SHDHPHPQPGDTSDLNYLQEQVGGMLKITPSDVENDESDYWLLSNAEISMTDIWKTDSGIDWDYGI
ADVSTPPPGMGEIAPTAVDSTPR
```

FIGURE 6

Nucleotide sequence (SEQ ID NO 3) and amino acid sequence (SEQ ID NO 4) of the Arabidopsis Dimerisation partner (DPa). Start and stop codons are in bold and underlined.

SEQ ID NO 3 ccggcaggtg tttgtttata gcgggaactc tcacccaaag taatttcatc tccgattttt
tttttttgg ttgttgttcg catctctgtg taataaaaag agtaaaacca aaaccctaga
aaaaaatctc catctttttt attccgccat tggaagatcg atcactgaga aggatgagta
tggagatgga gttgtttgtc actccagaga agcagaggca acatccttca gtgagcgttg
agaaaactcc agtgagaagg aaattgattg ttgatgatga ttctgaaatt ggatcagaga
agaaagggca atcaagaact tctggaggcg ggcttcgtca attcagtgtt atggtttgtc
agaagttgga agccaagaag ataactactt acaaggaggt tgcagacgaa attatttcag
attttgccac aattaagcaa aacgcagaga agcctttgaa tgaaaatgag tacaatgaga
agaacataag gcggagagtc tacgatgcgc tcaatgtgtt catggcgttg gatattattg
caagggataa aaaggaaatc cggtggaaag gacttcctat tacctgcaaa aaggatgtgg
aagaagtcaa gatggatcgt aataaagtta tgagcagtgt gcaaaagaag gctgcttttc
ttaaagagtt gagagaaaag gtctcaagtc ttgagagtct tatgtcgaga aatcaagaga
tggttgtgaa gactcaaggc ccagcagaag gatttacctt accattcatt ctacttgaga
caaaccctca cgcagtagtc gaaatcgaga tttctgaaga tatgcaactt gtacacctcg
acttcaatag cacacctttc tcggtccatg atgatgctta cattttgaaa ctgatgcaag
aacagaagca ggaacagaac agagtatctt cttcttcatc tacacatcac caatctcaac
atagctccgc tcattcttca tccagttctt gcattgcttc tggaacctca ggcccggttt
gctggaactc gggatccatt gatactcgct gaccgagctt ctattcccaa attcttcaag
aagaagaagt aatgatctaa ttggtatact aaaaaattat acatctggtt tagtgttcaa
ttgagagaga ctgtaaaatc aattcatagg ccaacaaatg tttgtttatc caattttcct
ttttattcga acttgatgcg atatttcaac ggaaacagaa actattgttt taaaccaaaa
aaaaaaaaaa aaaa

SEQ ID NO 4

MSMEMELFVTPEKQRQHPSVSVEKTPVRRKLIVDDDSEIGSEKKGQSRTSGGGLRQFSVMVCQKLE
AKKITTYKEVADEIISDFATIKQNAEKPLNENEYNEKNIRRRVYDALNVFMALDIIARDKKEIRWK
GLPITCKKDVEEVKMDRNKVMSSVQKKAAFLKELREKVSSLESLMSRNQEMVVKTQGPAEGFTLPF
ILLETNPHAVVEIEISEDMQLVHLDFNSTPFSVHDDAYILKLMQEQKQEQNRVSSSSSTHHQSQHS
SAHSSSSSCIASGTSGPVCWNSGSIDTR

FIGURE 7

SEQ ID NO 19 splice variant of E2Fa as represented in SEQ ID NO 1. The startcodon of this E2F is at position 410 (bold and underlined) and the stopcodon is at position 1861 (bold underlined). The corresponding protein sequence is represented as SEQ ID NO 20

SEQ ID NO 19 catcaatctcaaattcagatgcatcattataggaaatgctatcctttgaaaagtttccaactgtc
atcagtctttaggcattctggtttaaagttgaaatattttgtatttgtaggcgcaacgatactctc
atttcgagaagtaagcagcagtttccaacctttgtcggtggaaatattggcttgattacttccca
atcttccttcttccatatgtcgtcaaggacaattaacgacttagacatttccaacaattgatatag
ttcacgttggagtgtatattctgtcatctccaagattttcttttcttcttcctctttctctcacta
aaacccttgtttccttcactcgccgtcgcttttcccgtcatcggaatcttcaaattcgactctcgc
ttcactacgatccatgtccggtgtcgtacgatcttctcccggttcttctcagccgccaccgccgcc
gccgcaccatccaccgtcatctccggttccggttacatctacgccggttataccacctatacgtcg
tcacttagctttcgcctcaacaaacctccgtttcatccttccgatgattaccatcgatttaaccc
ttcttcgctcagtaataataacgacaggagcttcgttcatggttgtggtgttgtagatcggagga
agatgctgtcgttgttagatctccttcacgaaagagaaaggcgacaatggatatggttgttgctcc
atctaataatggattcacgagttctggtttcactaacatacctagcagtccctgtcaaactcctag
aaaagggggcagagtcaacatcaagtcaaaggccaaaggaaacaagtcaactcctcaaacacccat
ctcgacaaacgctggttctcctatcacacttactccatcaggaagttgtcgttatgacagttcttt
aggtctccttacaaaaaagttcgtcaatctaattaaacaagccaaagatggaatgctggacctaaa
caaagctgcagaaacattggaggtgcagaaacgacgtatatatgatattacaaacgttttggaggg
gatagatctcattgaaaagcctttcaagaatcgaatactttggaagggagttgatgcgtgtcctgg
cgatgaggatgctgacgtatctgtattacaggcagaaattgaaaacctcgccctcgaagagcaagc
attagacaaccaaatcagacaaacagaggaaagattaagagacctgagcgaaaatgaaaagaatca
gaaatggcttttgtaactgaagaggatatcaagagtttaccaggtttccagaaccagactctgat
agccgtcaaagctcctcatggcacaactttggaagtgcctgatccagatgaagcggctgaccaccc
acaaaggagatacaggatcattcttagaagtacaatgggacctattgacgtatacctcgtcagcga
atttgaagggaaattcgaagacacaaatgggagtggtgcagcaccaccagcatgcttgcctattgc
ttctagctcaggatctacaggacaccatgacatcgaagccttaactgttgacaacccagaaactgc
tattgtgtctcatgatcatcctcatcctcaacccggcgatacctctgatcttaattatttgcaaga
gcaagtaggaggaatgcttaagattactccctctgatgttgaaaatgatgagtcggactactggct
tctctcaaatgctgagattagcatgacggatatttggaaaactgactctggtatcgattgggatta
tggaatagccgacgtgagtactccaccaccaggaatgggcgaaatagcaccaacagctgttgactc
aaccccgagatgatcgaataccaagcacacttctcaacttctgatcccaaatgtgttacctcacaa
cactccctaaaatcatatacaaggagggagcaactacagaacgtgtatgaaccaatggcaggtgcg
ttccatacaatgtaccattagattatgattcatttatcgcctagagtgatgttgtagaggagcacc
gagaaactaatgtaagtttaacagagaatgtacttcatcggctgcattggtacactatttgattat
aatattttgaccg

FIGURE 8

SEQ ID NO 20

MSGVVRSSPGSSQPPPPPPHHPPSSPVPVTSTPVIPPIRRHLAFASTKPPFHPSDDYHRFNPSSLS
NNNDRSFVHGCGVVDREEDAVVVRSPSRKRKATMDMVVAPSNNGFTSSGFTNIPSSPCQTPRKGGR
VNIKSKAKGNKSTPQTPISTNAGSPITLTPSGSCRYDSSLGLLTKKFVNLIKQAKDGMLDLNKAAE
TLEVQKRRIYDITNVLEGIDLIEKPFKNRILWKGVDACPGDEDADVSVLQAEIENLALEEQALDNQ
IRQTEERLRDLSENEKNQKWLFVTEEDIKSLPGFQNQTLIAVKAPHGTTLEVPDPDEAADHPQRRY
RIILRSTMGPIDVYLVSEFEGKFEDTNGSGAAPPACLPIASSSGSTGHHDIEALTVDNPETAIVSH
DHPHPQPGDTSDLNYLQEQVGGMLKITPSDVENDESDYWLLSNAEISMTDIWKTDSGIDWDYGIAD
VSTPPPGMGEIAPTAVDSTPR

FIGURE 8 (continued)

Sequence alignment of E2Fa proteins. This figure illustrates the sequence difference between E2Fa of SEQ ID NO 2 and its splice variant E2Fa of SEQ ID NO 20 (= CDS 009 E2Fa). Its also shown that the SEQ ID NO 2 completely corresponds to the Genbank databae entry CAC15486.

```
                        1                                                  50
         CAC15486    (1) MSGVVRSSPGSSQPPPPPPHHPPSSPVPVTSTPVIPPIRRHLAFASTKPP
     CDS009 E2Fa     (1) MSGVVRSSPGSSQPPPPPPHHPPSSPVPVTSTPVIPPIRRHLAFASTKPP
SEQ ID NO 2 E2Fa     (1) MSGVVRSSPGSSQPPPPPPHHPPSSPVPVTSTPVIPPIRRHLAFASTKPP
                         51                                               100
         CAC15486   (51) FHPSDDYHRFNPSSLSNNNDRSFVHGCGVVDREEDAVVVRSPSRKRKATM
     CDS009 E2Fa    (51) FHPSDDYHRFNPSSLSNNNDRSFVHGCGVVDREEDAVVVRSPSRKRKATM
SEQ ID NO 2 E2Fa    (51) FHPSDDYHRFNPSSLSNNNDRSFVHGCGVVDREEDAVVVRSPSRKRKATM
                         101                                              150
         CAC15486  (101) DMVVAPSNNGFTSSGFTNIPSSPCQTPRKGGRVNIKSKAKGNKSTPQTPI
     CDS009 E2Fa   (101) DMVVAPSNNGFTSSGFTNIPSSPCQTPRKGGRVNIKSKAKGNKSTPQTPI
SEQ ID NO 2 E2Fa   (101) DMVVAPSNNGFTSSGFTNIPSSPCQTPRKGGRVNIKSKAKGNKSTPQTPI
                         151                                              200
         CAC15486  (151) STNAGSPITLTPSGSCRYDSSLGLLTKKFVNLIKQAKDGMLDLNKAAETL
     CDS009 E2Fa   (151) STNAGSPITLTPSGSCRYDSSLGLLTKKFVNLIKQAKDGMLDLNKAAETL
SEQ ID NO 2 E2Fa   (151) STNAGSPITLTPSGSCRYDSSLGLLTKKFVNLIKQAKDGMLDLNKAAETL
                         201                                              250
         CAC15486  (201) EVQKRRIYDITNVLEGIDLIEKPFKNRILWKGVDACPGDEDADVSVLQLQ
     CDS009 E2Fa   (201) EVQKRRIYDITNVLEGIDLIEKPFKNRILWKGVDACPGDEDADVSVL--Q
SEQ ID NO 2 E2Fa   (201) EVQKRRIYDITNVLEGIDLIEKPFKNRILWKGVDACPGDEDADVSVLQLQ

                         251                                              300
         CAC15486  (251) AEIENLALEEQALDNQIRQTEERLRDLSENEKNQKWLFVTEEDIKSLPGF
     CDS009 E2Fa   (249) AEIENLALEEQALDNQIRQTEERLRDLSENEKNQKWLFVTEEDIKSLPGF
SEQ ID NO 2 E2Fa   (251) AEIENLALEEQALDNQIRQTEERLRDLSENEKNQKWLFVTEEDIKSLPGF
                         301                                              350
         CAC15486  (301) QNQTLIAVKAPHGTTLEVPDPDEAADHPQRRYRIILRSTMGPIDVYLVSE
     CDS009 E2Fa   (299) QNQTLIAVKAPHGTTLEVPDPDEAADHPQRRYRIILRSTMGPIDVYLVSE
SEQ ID NO 2 E2Fa   (301) QNQTLIAVKAPHGTTLEVPDPDEAADHPQRRYRIILRSTMGPIDVYLVSE
                         351                                              400
         CAC15486  (351) FEGKFEDTNGSGAAPPACLPIASSSGSTGHHDIEALTVDNPETAIVSHDH
     CDS009 E2Fa   (349) FEGKFEDTNGSGAAPPACLPIASSSGSTGHHDIEALTVDNPETAIVSHDH
SEQ ID NO 2 E2Fa   (351) FEGKFEDTNGSGAAPPACLPIASSSGSTGHHDIEALTVDNPETAIVSHDH
                         401                                              450
         CAC15486  (401) PHPQPGDTSDLNYLQEQVGGMLKITPSDVENDESDYWLLSNAEISMTDIW
     CDS009 E2Fa   (399) PHPQPGDTSDLNYLQEQVGGMLKITPSDVENDESDYWLLSNAEISMTDIW
SEQ ID NO 2 E2Fa   (401) PHPQPGDTSDLNYLQEQVGGMLKITPSDVENDESDYWLLSNAEISMTDIW
                         451                              485
         CAC15486  (451) KTDSGIDWDYGIADVSTPPPGMGEIAPTAVDSTPR
     CDS009 E2Fa   (449) KTDSGIDWDYGIADVSTPPPGMGEIAPTAVDSTPR
SEQ ID NO 2 E2Fa   (451) KTDSGIDWDYGIADVSTPPPGMGEIAPTAVDSTPR
```

FIGURE 9

Sequence alignment of E2Fa genes. This figure illustrates the sequence difference between E2Fa of SEQ ID NO 1 and its splice variant E2Fa of SEQ ID NO 19 (= CDS 009 E2Fa). Its also shown that the SEQ ID NO 2 completely corresponds to the Genbank databae entry AJ294534.

```
                      1                                                50
   AJ294534      (1)  --------------------------------------------------
CDS009 E2Fa      (1)  CATCAATCTCAAATTCAGATGCATCATTATAGGAAATGCTATCCTTTGAA
SEQ ID NO 1      (1)  --------------------------------------------------
                      51                                              100
   AJ294534      (1)  --------------------------------------------------
CDS009 E2Fa     (51)  AAAGTTTCCAACTGTCATCAGTCTTTAGGCATTCTGGTTTAAAGTTGAAA
SEQ ID NO 1      (1)  --------------------------------------------------
                      101                                             150
   AJ294534      (1)  --------------------------------------------------
CDS009 E2Fa    (101)  TATTTTGTATTTGTAGGCGCAACGATACTCTCATTTCGAGAAGTAAGCAG
SEQ ID NO 1      (1)  --------------------------------------------------
                      151                                             200
   AJ294534      (1)  --------------------------------------------------
CDS009 E2Fa    (151)  CAGTTTCCAACCTTTTGTCGGTGGAAATATTGGCTTGATTACTTCCCAAT
SEQ ID NO 1      (1)  --------------------------------------------------
                      201                                             250
   AJ294534      (1)  --------------------------------------------------
CDS009 E2Fa    (201)  CTTCCTTCTTCCATATGTCGTCAAGGACAATTAACGACTTAGACATTTCC
SEQ ID NO 1      (1)  --------------------------------------------------
                      251                                             300
   AJ294534      (1)  --------------------------------------------------
CDS009 E2Fa    (251)  AACAATTGATATAGTTCACGTTGGAGTGTATATTCTGTCATCTCCAAGAT
SEQ ID NO 1      (1)  --------------------------------------------------
                      301                                             350
   AJ294534      (1)  --------------------------------------------------
CDS009 E2Fa    (301)  TTTCTTTTCTTCTTCCTCTTTCTCTCACTAAAACCCTTGTTTCCTTCACT
SEQ ID NO 1      (1)  --------------------------------------------------
                      351                                             400
   AJ294534      (1)  --------------------------------------------------
CDS009 E2Fa    (351)  CGCCGTCGCTTTTCCCGTCATCGGAATCTTCAAATTCGACTCTCGCTTCA
SEQ ID NO 1      (1)  --------------------------------------------------
                      401                                             450
   AJ294534      (1)  ---------ATGTCCGGTGTCGTACGATCTTCTCCCGGTTCTTCTCAGCC
CDS009 E2Fa    (401)  CTACGATCCATGTCCGGTGTCGTACGATCTTCTCCCGGTTCTTCTCAGCC
SEQ ID NO 1      (1)  ---------ATGTCCGGTGTCGTACGATCTTCTCCCGGTTCTTCTCAGCC
                      451                                             500
   AJ294534     (42)  GCCACCGCCGCCGCCGCACCATCCACCGTCATCTCCGGTTCCGGTTACAT
CDS009 E2Fa    (451)  GCCACCGCCGCCGCCGCACCATCCACCGTCATCTCCGGTTCCGGTTACAT
SEQ ID NO 1     (42)  GCCACCGCCGCCGCCGCACCATCCACCGTCATCTCCGGTTCCGGTTACAT
                      501                                             550
   AJ294534     (92)  CTACGCCGGTTATACCACCTATACGTCGTCACTTAGCTTTCGCCTCAACA
CDS009 E2Fa    (501)  CTACGCCGGTTATACCACCTATACGTCGTCACTTAGCTTTCGCCTCAACA
SEQ ID NO 1     (92)  CTACGCCGGTTATACCACCTATACGTCGTCACTTAGCTTTCGCCTCAACA
```

FIGURE 10

```
                       551                                              600
   AJ294534     (142)  AAACCTCCGTTTCATCCTTCCGATGATTACCATCGATTTAACCCTTCTTC
 CDS009 E2Fa    (551)  AAACCTCCGTTTCATCCTTCCGATGATTACCATCGATTTAACCCTTCTTC
 SEQ ID NO 1    (142)  AAACCTCCGTTTCATCCTTCCGATGATTACCATCGATTTAACCCTTCTTC
                       601                                              650
   AJ294534     (192)  GCTCAGTAATAATAACGACAGGAGCTTCGTTCATGGTTGTGGTGTTGTAG
 CDS009 E2Fa    (601)  GCTCAGTAATAATAACGACAGGAGCTTCGTTCATGGTTGTGGTGTTGTAG
 SEQ ID NO 1    (192)  GCTCAGTAATAATAACGACAGGAGCTTCGTTCATGGTTGTGGTGTTGTAG
                       651                                              700
   AJ294534     (242)  ATCGGGAGGAAGATGCTGTCGTTGTTAGATCTCCTTCACGAAAGAGAAAG
 CDS009 E2Fa    (651)  ATCGGGAGGAAGATGCTGTCGTTGTTAGATCTCCTTCACGAAAGAGAAAG
 SEQ ID NO 1    (242)  ATCGGGAGGAAGATGCTGTCGTTGTTAGATCTCCTTCACGAAAGAGAAAG
                       701                                              750
   AJ294534     (292)  GCGACAATGGATATGGTTGTTGCTCCATCTAATAATGGATTCACGAGTTC
 CDS009 E2Fa    (701)  GCGACAATGGATATGGTTGTTGCTCCATCTAATAATGGATTCACGAGTTC
 SEQ ID NO 1    (292)  GCGACAATGGATATGGTTGTTGCTCCATCTAATAATGGATTCACGAGTTC
                       751                                              800
   AJ294534     (342)  TGGTTTCACTAACATACCTAGCAGTCCCTGTCAAACTCCTAGAAAAGGGG
 CDS009 E2Fa    (751)  TGGTTTCACTAACATACCTAGCAGTCCCTGTCAAACTCCTAGAAAAGGGG
 SEQ ID NO 1    (342)  TGGTTTCACTAACATACCTAGCAGTCCCTGTCAAACTCCTAGAAAAGGGG
                       801                                              850
   AJ294534     (392)  GCAGAGTCAACATCAAGTCAAAGGCCAAAGGAAACAAGTCAACTCCTCAA
 CDS009 E2Fa    (801)  GCAGAGTCAACATCAAGTCAAAGGCCAAAGGAAACAAGTCAACTCCTCAA
 SEQ ID NO 1    (392)  GCAGAGTCAACATCAAGTCAAAGGCCAAAGGAAACAAGTCAACTCCTCAA
                       851                                              900
   AJ294534     (442)  ACACCCATCTCGACAAACGCTGGTTCTCCTATCACACTTACTCCATCAGG
 CDS009 E2Fa    (851)  ACACCCATCTCGACAAACGCTGGTTCTCCTATCACACTTACTCCATCAGG
 SEQ ID NO 1    (442)  ACACCCATCTCGACAAACGCTGGTTCTCCTATCACACTTACTCCATCAGG
                       901                                              950
   AJ294534     (492)  AAGTTGTCGTTATGACAGTTCTTTAGGTCTCCTTACAAAAAAGTTCGTCA
 CDS009 E2Fa    (901)  AAGTTGTCGTTATGACAGTTCTTTAGGTCTCCTTACAAAAAAGTTCGTCA
 SEQ ID NO 1    (492)  AAGTTGTCGTTATGACAGTTCTTTAGGTCTCCTTACAAAAAAGTTCGTCA
                       951                                             1000
   AJ294534     (542)  ATCTAATTAAACAAGCCAAAGATGGAATGCTGGACCTAAACAAAGCTGCA
 CDS009 E2Fa    (951)  ATCTAATTAAACAAGCCAAAGATGGAATGCTGGACCTAAACAAAGCTGCA
 SEQ ID NO 1    (542)  ATCTAATTAAACAAGCCAAAGATGGAATGCTGGACCTAAACAAAGCTGCA
                       1001                                            1050
   AJ294534     (592)  GAAACATTGGAGGTGCAGAAACGACGTATATATGATATTACAAACGTTTT
 CDS009 E2Fa   (1001)  GAAACATTGGAGGTGCAGAAACGACGTATATATGATATTACAAACGTTTT
 SEQ ID NO 1    (592)  GAAACATTGGAGGTGCAGAAACGACGTATATATGATATTACAAACGTTTT
                       1051                                            1100
   AJ294534     (642)  GGAGGGGATAGATCTCATTGAAAAGCCTTTCAAGAATCGAATACTTTGGA
 CDS009 E2Fa   (1051)  GGAGGGGATAGATCTCATTGAAAAGCCTTTCAAGAATCGAATACTTTGGA
 SEQ ID NO 1    (642)  GGAGGGGATAGATCTCATTGAAAAGCCTTTCAAGAATCGAATACTTTGGA
                       1101                                            1150
   AJ294534     (692)  AGGGAGTTGATGCGTGTCCTGGCGATGAGGATGCTGACGTATCTGTATTA
 CDS009 E2Fa   (1101)  AGGGAGTTGATGCGTGTCCTGGCGATGAGGATGCTGACGTATCTGTATTA
 SEQ ID NO 1    (692)  AGGGAGTTGATGCGTGTCCTGGCGATGAGGATGCTGACGTATCTGTATTA
```

FIGURE 10 (continued)

```
                              1151                                              1200
     AJ294534      (742)  CAGCTGCAGGCAGAAATTGAAAACCTCGCCCTCGAAGAGCAAGCATTAGA
  CDS009 E2Fa     (1151)  CAG------GCAGAAATTGAAAACCTCGCCCTCGAAGAGCAAGCATTAGA
  SEQ ID NO 1      (742)  CAGCTGCAGGCAGAAATTGAAAACCTCGCCCTCGAAGAGCAAGCATTAGA
                          1201                                              1250
     AJ294534      (792)  CAACCAAATCAGACAAACAGAGGAAAGATTAAGAGACCTGAGCGAAAATG
  CDS009 E2Fa     (1195)  CAACCAAATCAGACAAACAGAGGAAAGATTAAGAGACCTGAGCGAAAATG
  SEQ ID NO 1      (792)  CAACCAAATCAGACAAACAGAGGAAAGATTAAGAGACCTGAGCGAAAATG
                          1251                                              1300
     AJ294534      (842)  AAAAGAATCAGAAATGGCTTTTTGTAACTGAAGAGGATATCAAGAGTTTA
  CDS009 E2Fa     (1245)  AAAAGAATCAGAAATGGCTTTTTGTAACTGAAGAGGATATCAAGAGTTTA
  SEQ ID NO 1      (842)  AAAAGAATCAGAAATGGCTTTTTGTAACTGAAGAGGATATCAAGAGTTTA
                          1301                                              1350
     AJ294534      (892)  CCAGGTTTCCAGAACCAGACTCTGATAGCCGTCAAAGCTCCTCATGGCAC
  CDS009 E2Fa     (1295)  CCAGGTTTCCAGAACCAGACTCTGATAGCCGTCAAAGCTCCTCATGGCAC
  SEQ ID NO 1      (892)  CCAGGTTTCCAGAACCAGACTCTGATAGCCGTCAAAGCTCCTCATGGCAC
                          1351                                              1400
     AJ294534      (942)  AACTTTGGAAGTGCCTGATCCAGATGAAGCGGCTGACCACCCACAAAGGA
  CDS009 E2Fa     (1345)  AACTTTGGAAGTGCCTGATCCAGATGAAGCGGCTGACCACCCACAAAGGA
  SEQ ID NO 1      (942)  AACTTTGGAAGTGCCTGATCCAGATGAAGCGGCTGACCACCCACAAAGGA
                          1401                                              1450
     AJ294534      (992)  GATACAGGATCATTCTTAGAAGTACAATGGGACCTATTGACGTATACCTC
  CDS009 E2Fa     (1395)  GATACAGGATCATTCTTAGAAGTACAATGGGACCTATTGACGTATACCTC
  SEQ ID NO 1      (992)  GATACAGGATCATTCTTAGAAGTACAATGGGACCTATTGACGTATACCTC
                          1451                                              1500
     AJ294534     (1042)  GTCAGCGAATTTGAAGGGAAATTCGAAGACACAAATGGGAGTGGTGCAGC
  CDS009 E2Fa     (1445)  GTCAGCGAATTTGAAGGGAAATTCGAAGACACAAATGGGAGTGGTGCAGC
  SEQ ID NO 1     (1042)  GTCAGCGAATTTGAAGGGAAATTCGAAGACACAAATGGGAGTGGTGCAGC
                          1501                                              1550
     AJ294534     (1092)  ACCACCAGCATGCTTGCCTATTGCTTCTAGCTCAGGATCTACAGGACACC
  CDS009 E2Fa     (1495)  ACCACCAGCATGCTTGCCTATTGCTTCTAGCTCAGGATCTACAGGACACC
  SEQ ID NO 1     (1092)  ACCACCAGCATGCTTGCCTATTGCTTCTAGCTCAGGATCTACAGGACACC
                          1551                                              1600
     AJ294534     (1142)  ATGACATCGAAGCCTTAACTGTTGACAACCCAGAAACTGCTATTGTGTCT
  CDS009 E2Fa     (1545)  ATGACATCGAAGCCTTAACTGTTGACAACCCAGAAACTGCTATTGTGTCT
  SEQ ID NO 1     (1142)  ATGACATCGAAGCCTTAACTGTTGACAACCCAGAAACTGCTATTGTGTCT
                          1601                                              1650
     AJ294534     (1192)  CATGATCATCCTCATCCTCAACCCGGCGATACCTCTGATCTTAATTATTT
  CDS009 E2Fa     (1595)  CATGATCATCCTCATCCTCAACCCGGCGATACCTCTGATCTTAATTATTT
  SEQ ID NO 1     (1192)  CATGATCATCCTCATCCTCAACCCGGCGATACCTCTGATCTTAATTATTT
                          1651                                              1700
     AJ294534     (1242)  GCAAGAGCAAGTAGGAGGAATGCTTAAGATTACTCCCTCTGATGTTGAAA
  CDS009 E2Fa     (1645)  GCAAGAGCAAGTAGGAGGAATGCTTAAGATTACTCCCTCTGATGTTGAAA
  SEQ ID NO 1     (1242)  GCAAGAGCAAGTAGGAGGAATGCTTAAGATTACTCCCTCTGATGTTGAAA
                          1701                                              1750
     AJ294534     (1292)  ATGATGAGTCGGACTACTGGCTTCTCTCAAATGCTGAGATTAGCATGACG
  CDS009 E2Fa     (1695)  ATGATGAGTCGGACTACTGGCTTCTCTCAAATGCTGAGATTAGCATGACG
  SEQ ID NO 1     (1292)  ATGATGAGTCGGACTACTGGCTTCTCTCAAATGCTGAGATTAGCATGACG
```

FIGURE 10 (continued)

```
                      1751                                           1800
   AJ294534  (1342)  GATATTTGGAAAACTGACTCTGGTATCGATTGGGATTATGGAATAGCCGA
CDS009 E2Fa  (1745)  GATATTTGGAAAACTGACTCTGGTATCGATTGGGATTATGGAATAGCCGA
SEQ ID NO 1  (1342)  GATATTTGGAAAACTGACTCTGGTATCGATTGGGATTATGGAATAGCCGA
                      1801                                           1850
   AJ294534  (1392)  CGTGAGTACTCCACCACCAGGAATGGGCGAAATAGCACCAACAGCTGTTG
CDS009 E2Fa  (1795)  CGTGAGTACTCCACCACCAGGAATGGGCGAAATAGCACCAACAGCTGTTG
SEQ ID NO 1  (1392)  CGTGAGTACTCCACCACCAGGAATGGGCGAAATAGCACCAACAGCTGTTG
                      1851                                           1900
   AJ294534  (1442)  ACTCAACCCCGAGATGA---------------------------------
CDS009 E2Fa  (1845)  ACTCAACCCCGAGATGATCGAATACCAAGCACACTTCTCAACTTCTGATC
SEQ ID NO 1  (1442)  ACTCAACCCCGAGATGA---------------------------------
                      1901                                           1950
   AJ294534  (1459)  --------------------------------------------------
CDS009 E2Fa  (1895)  CCAAATGTGTTACCTCACAACACTCCCTAAAATCATATACAAGGAGGGAG
SEQ ID NO 1  (1459)  --------------------------------------------------
                      1951                                           2000
   AJ294534  (1459)  --------------------------------------------------
CDS009 E2Fa  (1945)  CAACTACAGAACGTGTATGAACCAATGGCAGGTGCGTTCCATACAATGTA
SEQ ID NO 1  (1459)  --------------------------------------------------
                      2001                                           2050
   AJ294534  (1459)  --------------------------------------------------
CDS009 E2Fa  (1995)  CCATTAGATTATGATTCATTTATCGCCTAGAGTGATGTTGTAGAGGAGCA
SEQ ID NO 1  (1459)  --------------------------------------------------
                      2051                                           2100
   AJ294534  (1459)  --------------------------------------------------
CDS009 E2Fa  (2045)  CCGAGAAACTAATGTAAGTTTAACAGAGAATGTACTTCATCGGCTGCATT
SEQ ID NO 1  (1459)  --------------------------------------------------
                      2101                          2132
   AJ294534  (1459)  --------------------------------
CDS009 E2Fa  (2095)  GGTACACTATTTGATTATAATATTTTTGACCG
SEQ ID NO 1  (1459)  --------------------------------
```

FIGURE 10 (continued)

SEQUENCE LISTING

```
<160> NUMBER OF SEQ ID NOS: 22

<210> SEQ ID NO 1
<211> LENGTH: 1458
<212> TYPE: DNA
<213> ORGANISM: Arabidopsis thaliana

<400> SEQUENCE: 1

atgtccggtg tcgtacgatc ttctcccggt tcttctcagc cgccaccgcc gccgccgcac     60

catccaccgt catctccggt tccggttaca tctacgccgg ttataccacc tatacgtcgt    120

cacttagctt tcgcctcaac aaaacctccg tttcatcctt ccgatgatta ccatcgattt    180

aacccttctt cgctcagtaa taataacgac aggagcttcg ttcatggttg tggtgttgta    240

gatcgggagg aagatgctgt cgttgttaga tctccttcac gaaagagaaa ggcgacaatg    300

gatatggttg ttgctccatc taataatgga ttcacgagtt ctggtttcac taacatacct    360

agcagtccct gtcaaactcc tagaaaaggg ggcagagtca acatcaagtc aaaggccaaa    420

ggaaacaagt caactcctca aacacccatc tcgacaaacg ctggttctcc tatcacactt    480

actccatcag gaagttgtcg ttatgacagt tctttaggtc tccttacaaa aaagttcgtc    540

aatctaatta aacaagccaa agatggaatg ctggacctaa acaaagctgc agaaacattg    600

gaggtgcaga aacgacgtat atatgatatt acaaacgttt tggaggggat agatctcatt    660

gaaaagcctt tcaagaatcg aatactttgg aagggagttg atgcgtgtcc tggcgatgag    720

gatgctgacg tatctgtatt acagctgcag gcagaaattg aaaacctcgc cctcgaagag    780

caagcattag acaaccaaat cagacaaaca gaggaaagat taagagacct gagcgaaaat    840

gaaaagaatc agaaatggct tttgtaact gaagaggata tcaagagttt accaggtttc    900

cagaaccaga ctctgatagc cgtcaaagct cctcatggca caactttgga agtgcctgat    960

ccagatgaag cggctgacca cccacaaagg agatacagga tcattcttag aagtacaatg   1020

ggacctattg acgtatacct cgtcagcgaa tttgaaggga aattcgaaga cacaaatggg   1080

agtggtgcag caccaccagc atgcttgcct attgcttcta gctcaggatc tacaggacac   1140

catgacatcg aagccttaac tgttgacaac ccagaaactg ctattgtgtc tcatgatcat   1200

cctcatcctc aacccggcga tacctctgat cttaattatt tgcaagagca agtaggagga   1260

atgcttaaga ttactccctc tgatgttgaa aatgatgagt cggactactg gcttctctca   1320

aatgctgaga ttagcatgac ggatatttgg aaaactgact ctggtatcga ttgggattat   1380

ggaatagccg acgtgagtac tccaccacca ggaatgggcg aaatagcacc aacagctgtt   1440

gactcaaccc cgagatga                                                 1458

<210> SEQ ID NO 2
<211> LENGTH: 485
<212> TYPE: PRT
<213> ORGANISM: Arabidopsis thaliana

<400> SEQUENCE: 2
```

-continued

```
Met Ser Gly Val Val Arg Ser Ser Pro Gly Ser Ser Gln Pro Pro Pro
1               5                   10                  15

Pro Pro Pro His His Pro Pro Ser Ser Pro Val Pro Val Thr Ser Thr
            20                  25                  30

Pro Val Ile Pro Pro Ile Arg Arg His Leu Ala Phe Ala Ser Thr Lys
        35                  40                  45

Pro Pro Phe His Pro Ser Asp Asp Tyr His Arg Phe Asn Pro Ser Ser
    50                  55                  60

Leu Ser Asn Asn Asn Asp Arg Ser Phe Val His Gly Cys Gly Val Val
65                  70                  75                  80

Asp Arg Glu Glu Asp Ala Val Val Val Arg Ser Pro Ser Arg Lys Arg
                85                  90                  95

Lys Ala Thr Met Asp Met Val Val Ala Pro Ser Asn Asn Gly Phe Thr
            100                 105                 110

Ser Ser Gly Phe Thr Asn Ile Pro Ser Ser Pro Cys Gln Thr Pro Arg
        115                 120                 125

Lys Gly Gly Arg Val Asn Ile Lys Ser Lys Ala Lys Gly Asn Lys Ser
    130                 135                 140

Thr Pro Gln Thr Pro Ile Ser Thr Asn Ala Gly Ser Pro Ile Thr Leu
145                 150                 155                 160

Thr Pro Ser Gly Ser Cys Arg Tyr Asp Ser Ser Leu Gly Leu Leu Thr
                165                 170                 175

Lys Lys Phe Val Asn Leu Ile Lys Gln Ala Lys Asp Gly Met Leu Asp
            180                 185                 190

Leu Asn Lys Ala Ala Glu Thr Leu Glu Val Gln Lys Arg Arg Ile Tyr
        195                 200                 205

Asp Ile Thr Asn Val Leu Glu Gly Ile Asp Leu Ile Glu Lys Pro Phe
    210                 215                 220

Lys Asn Arg Ile Leu Trp Lys Gly Val Asp Ala Cys Pro Gly Asp Glu
225                 230                 235                 240

Asp Ala Asp Val Ser Val Leu Gln Leu Gln Ala Glu Ile Glu Asn Leu
                245                 250                 255

Ala Leu Glu Glu Gln Ala Leu Asp Asn Gln Ile Arg Gln Thr Glu Glu
            260                 265                 270

Arg Leu Arg Asp Leu Ser Glu Asn Glu Lys Asn Gln Lys Trp Leu Phe
        275                 280                 285

Val Thr Glu Glu Asp Ile Lys Ser Leu Pro Gly Phe Gln Asn Gln Thr
    290                 295                 300

Leu Ile Ala Val Lys Ala Pro His Gly Thr Thr Leu Glu Val Pro Asp
305                 310                 315                 320

Pro Asp Glu Ala Ala Asp His Pro Gln Arg Arg Tyr Arg Ile Ile Leu
                325                 330                 335

Arg Ser Thr Met Gly Pro Ile Asp Val Tyr Leu Val Ser Glu Phe Glu
            340                 345                 350

Gly Lys Phe Glu Asp Thr Asn Gly Ser Gly Ala Ala Pro Pro Ala Cys
        355                 360                 365

Leu Pro Ile Ala Ser Ser Ser Gly Ser Thr Gly His His Asp Ile Glu
    370                 375                 380

Ala Leu Thr Val Asp Asn Pro Glu Thr Ala Ile Val Ser His Asp His
385                 390                 395                 400

Pro His Pro Gln Pro Gly Asp Thr Ser Asp Leu Asn Tyr Leu Gln Glu
                405                 410                 415
```

-continued

```
Gln Val Gly Gly Met Leu Lys Ile Thr Pro Ser Asp Val Glu Asn Asp
            420                 425                 430

Glu Ser Asp Tyr Trp Leu Leu Ser Asn Ala Glu Ile Ser Met Thr Asp
        435                 440                 445

Ile Trp Lys Thr Asp Ser Gly Ile Asp Trp Asp Tyr Gly Ile Ala Asp
    450                 455                 460

Val Ser Thr Pro Pro Pro Gly Met Gly Glu Ile Ala Pro Thr Ala Val
465                 470                 475                 480

Asp Ser Thr Pro Arg
                485


<210> SEQ ID NO 3
<211> LENGTH: 1274
<212> TYPE: DNA
<213> ORGANISM: Arabidopsis thaliana

<400> SEQUENCE: 3

ccggcaggtg tttgtttata gcgggaactc tcacccaaag taatttcatc tccgattttt     60

tttttttgg ttgttgttcg catctctgtg taataaaaag agtaaaacca aaaccctaga    120

aaaaaatctc catctttttt attccgccat tggaagatcg atcactgaga aggatgagta    180

tggagatgga gttgtttgtc actccagaga agcagaggca acatccttca gtgagcgttg    240

agaaaactcc agtgagaagg aaattgattg ttgatgatga ttctgaaatt ggatcagaga    300

agaaagggca atcaagaact tctggaggcg ggcttcgtca attcagtgtt atggtttgtc    360

agaagttgga agccaagaag ataactactt acaaggaggt tgcagacgaa attatttcag    420

attttgccac aattaagcaa aacgcagaga agcctttgaa tgaaaatgag tacaatgaga    480

agaacataag gcggagagtc tacgatgcgc tcaatgtgtt catggcgttg gatattattg    540

caagggataa aaaggaaatc cggtggaaag gacttcctat tacctgcaaa aaggatgtgg    600

aagaagtcaa gatggatcgt aataaagtta tgagcagtgt gcaaaagaag gctgcttttc    660

ttaaagagtt gagagaaaag gtctcaagtc ttgagagtct tatgtcgaga aatcaagaga    720

tggttgtgaa gactcaaggc ccagcagaag gatttacctt accattcatt ctacttgaga    780

caaaccctca cgcagtagtc gaaatcgaga tttctgaaga tatgcaactt gtacacctcg    840

acttcaatag cacacctttc tcggtccatg atgatgctta cattttgaaa ctgatgcaag    900

aacagaagca ggaacagaac agagtatctt cttcttcatc tacacatcac caatctcaac    960

atagctccgc tcattcttca tccagttctt gcattgcttc tggaacctca ggcccggttt   1020

gctggaactc gggatccatt gatactcgct gaccgagctt ctattcccaa attcttcaag   1080

aagaagaagt aatgatctaa ttggtatact aaaaaattat acatctggtt tagtgttcaa   1140

ttgagagaga ctgtaaaatc aattcatagg ccaacaaatg tttgtttatc caattttcct   1200

ttttattcga acttgatgcg atatttcaac ggaaacagaa actattgttt taaaccaaaa   1260

aaaaaaaaaa aaaa                                                     1274


<210> SEQ ID NO 4
<211> LENGTH: 292
<212> TYPE: PRT
<213> ORGANISM: Arabidopsis thaliana

<400> SEQUENCE: 4

Met Ser Met Glu Met Glu Leu Phe Val Thr Pro Glu Lys Gln Arg Gln
1               5                   10                  15

His Pro Ser Val Ser Val Glu Lys Thr Pro Val Arg Arg Lys Leu Ile
```

-continued

```
            20                  25                  30

Val Asp Asp Asp Ser Glu Ile Gly Ser Glu Lys Lys Gly Gln Ser Arg
        35                  40                  45

Thr Ser Gly Gly Gly Leu Arg Gln Phe Ser Val Met Val Cys Gln Lys
    50                  55                  60

Leu Glu Ala Lys Lys Ile Thr Thr Tyr Lys Glu Val Ala Asp Glu Ile
65                  70                  75                  80

Ile Ser Asp Phe Ala Thr Ile Lys Gln Asn Ala Glu Lys Pro Leu Asn
                85                  90                  95

Glu Asn Glu Tyr Asn Glu Lys Asn Ile Arg Arg Arg Val Tyr Asp Ala
            100                 105                 110

Leu Asn Val Phe Met Ala Leu Asp Ile Ile Ala Arg Asp Lys Lys Glu
        115                 120                 125

Ile Arg Trp Lys Gly Leu Pro Ile Thr Cys Lys Lys Asp Val Glu Glu
    130                 135                 140

Val Lys Met Asp Arg Asn Lys Val Met Ser Ser Val Gln Lys Lys Ala
145                 150                 155                 160

Ala Phe Leu Lys Glu Leu Arg Glu Lys Val Ser Ser Leu Glu Ser Leu
                165                 170                 175

Met Ser Arg Asn Gln Glu Met Val Val Lys Thr Gln Gly Pro Ala Glu
            180                 185                 190

Gly Phe Thr Leu Pro Phe Ile Leu Leu Glu Thr Asn Pro His Ala Val
        195                 200                 205

Val Glu Ile Glu Ile Ser Glu Asp Met Gln Leu Val His Leu Asp Phe
    210                 215                 220

Asn Ser Thr Pro Phe Ser Val His Asp Asp Ala Tyr Ile Leu Lys Leu
225                 230                 235                 240

Met Gln Glu Gln Lys Gln Glu Gln Asn Arg Val Ser Ser Ser Ser Ser
                245                 250                 255

Thr His His Gln Ser Gln His Ser Ser Ala His Ser Ser Ser Ser Ser
            260                 265                 270

Cys Ile Ala Ser Gly Thr Ser Gly Pro Val Cys Trp Asn Ser Gly Ser
        275                 280                 285

Ile Asp Thr Arg
    290


<210> SEQ ID NO 5
<211> LENGTH: 33
<212> TYPE: DNA
<213> ORGANISM: Artificial Sequence
<220> FEATURE:
<223> OTHER INFORMATION: primer

<400> SEQUENCE: 5

ggccatggcc ggtgtcgtac gatcttctcc cga                                33


<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6

ggggatcctc atctcggggt tgagt                                         25


<210> SEQ ID NO 7
```

<211> LENGTH: 24
<212> TYPE: DNA
<213> ORGANISM: Artificial Sequence
<220> FEATURE:
<223> OTHER INFORMATION: primer

<400> SEQUENCE: 7
ggccatggag ttgtttgtca ctcc 24

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
ggagatcttc agcgagtatc aatgg 25

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
tatggctgtc tggggtttc 19

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
caacttgaac gtgtggttgg 20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
tcgagtcggt tggaagaaag 20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
ctcatgaacc atagccgtca 20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gcaccgtcaa ctgttgtttg 20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
caagcctctc ctgcagaatc 20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
aggctaatga gggaggggta 20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
ggaactggcc tcatttgtgt 20

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
gtgccaatct acgagggttt c 21

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
caatgggact aaaacgaaaa 20

<210> SEQ ID NO 19
<211> LENGTH: 2126
<212> TYPE: DNA
<213> ORGANISM: Arabidopsis thaliana

<400> SEQUENCE: 19
catcaatctc aaattcagat gcatcattat aggaaatgct atcctttgaa aaagtttcca 60
actgtcatca gtctttaggc attctggttt aaagttgaaa tattttgtat ttgtaggcgc 120
aacgatactc tcatttcgag aagtaagcag cagtttccaa ccttttgtcg gtggaaatat 180
tggcttgatt acttcccaat cttccttctt ccatatgtcg tcaaggacaa ttaacgactt 240

-continued

```
agacatttcc aacaattgat atagttcacg ttggagtgta tattctgtca tctccaagat    300
tttcttttct tcttcctctt tctctcacta aaacccttgt ttccttcact cgccgtcgct    360
tttcccgtca tcggaatctt caaattcgac tctcgcttca ctacgatcca tgtccggtgt    420
cgtacgatct tctcccggtt cttctcagcc gccaccgccg ccgccgcacc atccaccgtc    480
atctccggtt ccggttacat ctacgccggt tataccacct atacgtcgtc acttagcttt    540
cgcctcaaca aaacctccgt ttcatccttc cgatgattac catcgattta acccttcttc    600
gctcagtaat aataacgaca ggagcttcgt tcatggttgt ggtgttgtag atcgggagga    660
agatgctgtc gttgttagat ctccttcacg aaagagaaag gcgacaatgg atatggttgt    720
tgctccatct aataatggat tcacgagttc tggtttcact aacataccta gcagtccctg    780
tcaaactcct agaaaagggg gcagagtcaa catcaagtca aaggccaaag gaaacaagtc    840
aactcctcaa acacccatct cgacaaacgc tggttctcct atcacactta ctccatcagg    900
aagttgtcgt tatgacagtt ctttaggtct ccttacaaaa aagttcgtca atctaattaa    960
acaagccaaa gatggaatgc tggacctaaa caaagctgca gaaacattgg aggtgcagaa   1020
acgacgtata tatgatatta caaacgtttt ggaggggata gatctcattg aaaagccttt   1080
caagaatcga atactttgga agggagttga tgcgtgtcct ggcgatgagg atgctgacgt   1140
atctgtatta caggcagaaa ttgaaaacct cgccctcgaa gagcaagcat tagacaacca   1200
aatcagacaa acagaggaaa gattaagaga cctgagcgaa aatgaaaaga atcagaaatg   1260
gctttttgta actgaagagg atatcaagag tttaccaggt ttccagaacc agactctgat   1320
agccgtcaaa gctcctcatg gcacaacttt ggaagtgcct gatccagatg aagcggctga   1380
ccacccacaa aggagataca ggatcattct tagaagtaca atgggaccta ttgacgtata   1440
cctcgtcagc gaatttgaag ggaaattcga agacacaaat gggagtggtg cagcaccacc   1500
agcatgcttg cctattgctt ctagctcagg atctacagga caccatgaca tcgaagcctt   1560
aactgttgac aacccagaaa ctgctattgt gtctcatgat catcctcatc ctcaacccgg   1620
cgatacctct gatcttaatt atttgcaaga gcaagtagga ggaatgctta agattactcc   1680
ctctgatgtt gaaaatgatg agtcggacta ctggcttctc tcaaatgctg agattagcat   1740
gacggatatt tggaaaactg actctggtat cgattgggat tatggaatag ccgacgtgag   1800
tactccacca ccaggaatgg gcgaaatagc accaacagct gttgactcaa ccccgagatg   1860
atcgaatacc aagcacactt ctcaacttct gatcccaaat gtgttacctc acaacactcc   1920
ctaaaatcat atacaaggag ggagcaacta cagaacgtgt atgaaccaat ggcaggtgcg   1980
ttccatacaa tgtaccatta gattatgatt catttatcgc ctagagtgat gttgtagagg   2040
agcaccgaga aactaatgta agtttaacag agaatgtact tcatcggctg cattggtaca   2100
ctatttgatt ataatatttt tgaccg                                         2126
```

<210> SEQ ID NO 20
<211> LENGTH: 483
<212> TYPE: PRT
<213> ORGANISM: Arabidopsis thaliana

<400> SEQUENCE: 20

```
Met Ser Gly Val Val Arg Ser Ser Pro Gly Ser Ser Gln Pro Pro Pro
1               5                   10                  15

Pro Pro Pro His His Pro Pro Ser Ser Pro Val Pro Val Thr Ser Thr
            20                  25                  30

Pro Val Ile Pro Pro Ile Arg Arg His Leu Ala Phe Ala Ser Thr Lys
```

-continued

```
        35                  40                  45

Pro Pro Phe His Pro Ser Asp Asp Tyr His Arg Phe Asn Pro Ser Ser
    50                  55                  60

Leu Ser Asn Asn Asn Asp Arg Ser Phe Val His Gly Cys Gly Val Val
65                  70                  75                  80

Asp Arg Glu Glu Asp Ala Val Val Val Arg Ser Pro Ser Arg Lys Arg
                85                  90                  95

Lys Ala Thr Met Asp Met Val Val Ala Pro Ser Asn Asn Gly Phe Thr
            100                 105                 110

Ser Ser Gly Phe Thr Asn Ile Pro Ser Ser Pro Cys Gln Thr Pro Arg
        115                 120                 125

Lys Gly Gly Arg Val Asn Ile Lys Ser Lys Ala Lys Gly Asn Lys Ser
    130                 135                 140

Thr Pro Gln Thr Pro Ile Ser Thr Asn Ala Gly Ser Pro Ile Thr Leu
145                 150                 155                 160

Thr Pro Ser Gly Ser Cys Arg Tyr Asp Ser Ser Leu Gly Leu Leu Thr
                165                 170                 175

Lys Lys Phe Val Asn Leu Ile Lys Gln Ala Lys Asp Gly Met Leu Asp
            180                 185                 190

Leu Asn Lys Ala Ala Glu Thr Leu Glu Val Gln Lys Arg Arg Ile Tyr
        195                 200                 205

Asp Ile Thr Asn Val Leu Glu Gly Ile Asp Leu Ile Glu Lys Pro Phe
    210                 215                 220

Lys Asn Arg Ile Leu Trp Lys Gly Val Asp Ala Cys Pro Gly Asp Glu
225                 230                 235                 240

Asp Ala Asp Val Ser Val Leu Gln Ala Glu Ile Glu Asn Leu Ala Leu
                245                 250                 255

Glu Glu Gln Ala Leu Asp Asn Gln Ile Arg Gln Thr Glu Glu Arg Leu
            260                 265                 270

Arg Asp Leu Ser Glu Asn Glu Lys Asn Gln Lys Trp Leu Phe Val Thr
        275                 280                 285

Glu Glu Asp Ile Lys Ser Leu Pro Gly Phe Gln Asn Gln Thr Leu Ile
    290                 295                 300

Ala Val Lys Ala Pro His Gly Thr Thr Leu Glu Val Pro Asp Pro Asp
305                 310                 315                 320

Glu Ala Ala Asp His Pro Gln Arg Arg Tyr Arg Ile Ile Leu Arg Ser
                325                 330                 335

Thr Met Gly Pro Ile Asp Val Tyr Leu Val Ser Glu Phe Glu Gly Lys
            340                 345                 350

Phe Glu Asp Thr Asn Gly Ser Gly Ala Ala Pro Pro Ala Cys Leu Pro
        355                 360                 365

Ile Ala Ser Ser Ser Gly Ser Thr Gly His His Asp Ile Glu Ala Leu
    370                 375                 380

Thr Val Asp Asn Pro Glu Thr Ala Ile Val Ser His Asp His Pro His
385                 390                 395                 400

Pro Gln Pro Gly Asp Thr Ser Asp Leu Asn Tyr Leu Gln Glu Gln Val
                405                 410                 415

Gly Gly Met Leu Lys Ile Thr Pro Ser Asp Val Glu Asn Asp Glu Ser
            420                 425                 430

Asp Tyr Trp Leu Leu Ser Asn Ala Glu Ile Ser Met Thr Asp Ile Trp
        435                 440                 445

Lys Thr Asp Ser Gly Ile Asp Trp Asp Tyr Gly Ile Ala Asp Val Ser
    450                 455                 460
```

-continued

```
Thr Pro Pro Pro Gly Met Gly Glu Ile Ala Pro Thr Ala Val Asp Ser
465                 470                 475                 480

Thr Pro Arg


<210> SEQ ID NO 21
<211> LENGTH: 56
<212> TYPE: DNA
<213> ORGANISM: Arabidopsis thaliana

<400> SEQUENCE: 21

ggggacaagt ttgtacaaaa aagcaggctt cacaatgtat tgctcttctt cgatgc         56


<210> SEQ ID NO 22
<211> LENGTH: 52
<212> TYPE: DNA
<213> ORGANISM: Arabidopsis thaliana

<400> SEQUENCE: 22

ggggaccact ttgtacaaga aagctgggtg cttggtgtca tcttgagaat ag             52
```

METHOD TO MODIFY CELL NUMBER, ARCHITECTURE AND YIELD OF PLANTS BY OVEREXPRESSING THE E2F TRANSCRIPTION FACTOR

CROSS REFERENCE TO RELATED APPLICATIONS

This application is a section 371 application of PCT International application No. PCT/EP02/10236, having an International Filing Date of Sep. 12, 2002, which claims priority of European Application No. 01870198.7, filed Sep. 14, 2001.

FIELD OF THE INVENTION

The present invention relates to the field of modifying plant yield and/or architecture by modulating cell cycle regulation comprising modulating expression of plant E2F transcription factors or modulating the complex of E2F with its dimerisation partner DP.

BACKGROUND TO THE INVENTION

Growth, development and differentiation of higher organisms is controlled by a highly ordered set of events called the cell cycle (Morgan, 1997). Cell division and cell growth are operated by the cell cycle which ensures correct timing and high fidelity of the different transition events involved. Transition control through and between the different stages of the mitotic cell cycle depend on the activity of cyclin-dependent kinases (CDKs) and their specific subset of cyclins and appears to be conserved in all higher eukaryotes (as the enzymes responsible for DNA replication, the cytoskeleton components that mediate spatial organization within and directed movements of the cell or its contents and the ubiquitin-dependent pathway for the degradation of proteins).

In multicellular eukaryotes, the association of multiple CDKs with different classes of cyclins called mitotic and G1 cyclins allows for the formation of various protein kinase complexes, each required for specific regulatory steps during the cell cycle.

The understanding of the cell cycle progression remains far better in the yeast and mammal model systems from which it was further elucidated that CDK activity is additionally regulated by factors including CDK kinases like the yeast Wee1-type kinases, CDK phosphatases like yeast CDC25, CDK inhibitors like the yeast SIC1 and the human INK4 gene products, and CDK activating kinase (CAK). Cell cycle regulation at both G1→S and G2→M phase transitions depends on the appropriate CDK-cyclin complexes; both transitions are believed to be the major control points in the cell cycle. The cell's decision to proliferate and synthesize DNA and ultimately to divide is made at the G1→S restriction point in late G1. Overcoming this point of no return needs the cell's competence to initiate DNA synthesis as well as the expression of S-phase genes. Transcription of S-phase specific genes requires binding to the DNA of an E2F transcription factor. The heterodimeric E2F/dimerization partner (DP) transcription factor regulates the promoter activity of multiple genes, which are essential for DNA replication and cell cycle control (Helin, 1998; Müller and Helin, 2000). E2F/DP activity is inhibited by the retinoblastoma gene product (Rb) that is regulated by phosphorylation (Weinberg, 1995). E2F transcription factors are critical effectors of the decision to pass the restriction point and to allow the cell to proceed in S-phase.

In plants, post-embryonic development relies on iterative cell division in the meristems. Cells in the meristem remain in an indeterminate state whereas upon differentiation they exit the cell cycle and move from the meristem. In the plant's meristematic or undifferentiated cell system the G1→S transition is characterized by the action of CDK-cyclin complexes involving D-type cyclins. Similar with the mammalian system, phosphorylation of the retinoblastoma protein by the CycD-CDK complex is required to release the associated E2F transcription factor, thereby enforcing the cell's commitment to S-phase and thus the cell's decision to pass over the cell cycle exit point. Thus, plant E2F and DP genes have been identified suggesting their involvement in the G1→S regulatory mechanism (Ramirez-Parra et al., 1999; Sekine et al., 1999; Ramirez-Parra and Gutierez, 2000; Magyar et al., 2000). Their role in the plant cell cycle molecular machinery that controls cell cycle exit and differentiation is still largely unknown. Therefore, one of the objects of the present invention is to identify the regulatory capacity on cell cycle progression of E2F transcription factors by modulating their expression in a plant. Modulating expression of these transcription factors allows manipulating the biological processes that they control. It is a further object of the present invention to modulate these biological processes towards particular useful applications in agriculture and horticulture. The invention provides a solution to at least several of the objects above by providing the embodiments described further.

SUMMARY OF THE INVENTION

In the present invention, the effect of E2Fa and E2Fa/DPa overexpression in plants is disclosed.

The present invention generally relates to a method for modifying plant developmental and/or growth processes, such as modulating the number of cells in a particular tissue such as for example the cotyledons or the meristems or the seeds. Also the present invention relates to altering plant architecture, such as or altering the size and number of particular plant organs, such as for example cotyledons, leaves, shoots, stem, tillers, panicles, ears, flowers, seeds, roots, tubers. Further the present invention relates to methods for altering plant growth rate, and/or stress-induced responses, and/or plant performance, and/or yield, said method comprising modulating the expression and/or activity of an E2F transcription factor or a homologue or a derivative thereof or an enzymatically active fragment thereof, alone or in combination with its dimerization partner (DP). In a particular embodiment of the present invention a gene encoding an E2F is placed under the control of a constitutive promoter or a regulatable promoter, preferably a cell- or tissue- or organ-specific promoter, and introduced into a plant. The present invention extends to the use of genetic constructs for performing the methods of the invention and to transgenic plants produced therewith having altered growth and/or development and/or architecture and/or physiological characteristics compared to their otherwise isogenic counterpart.

DETAILED DESCRIPTION OF THE INVENTION

In the present invention the effects obtained by transforming a plant with a E2F gene is shown for the first time. The inventors showed that plants transformed with an E2Fa gene showed increased cell numbers in certain organs and/or increased size of organs, for example enlarged cotyledons, and/or increased number of organs such a more tillers and panicles, compared to the plants not transformed with an E2F transcription factor.

According to a first embodiment, the present invention relates to a method for increasing the cell number of specific cell types, specific tissues or specific organs in a plant comprising modulating the expression and/or the activity in said specific cell types, specific tissues or specific organs of a plant E2F transcription factor.

In the description whenever the expression "modulating the expression and/or the activity of a plant E2F transcription factor" is used, a "plant E2F transcription factor" as used in this expression relates both to a gene or nucleic acid encoding a plant E2F transcription factor or a homologue or a derivative thereof or an enzymatically active fragment of an E2F encoding nucleic acid or gene, as well as it relates to the E2F protein, polypeptide or a homologue or a derivative or an enzymatically active fragment of the E2F protein or polypeptide.

The expression "modulating the expression" of an E2F transcription factor, for instance relates to methods for altering the expression of at least one nucleic acid in specific cells or tissues. According to the invention, the "nucleic acid" may be the wild type endogenic nucleic acid which expression is modulated or may be a nucleic acid derived from the same or another species but, in case of originating from the same species may be substantially modified from its native form in composition and/or genomic environment.

One way of modulating the expression of E2F transcription factors according to the invention relates to a method comprising the stable integration into the genome of a plant or in specific plant cells or tissues of said plant of an expressible nucleic acid encoding a plant E2F transcription factor, a homologue or a derivative thereof or an enzymatically active fragment thereof.

In the latter case, the term "expression" or "overexpression" should be understood as "ectopic expression". "Ectopic expression" or "ectopic overexpression" of a gene or a protein refers to expression patterns and/or expression levels of said gene or protein normally not occurring under natural conditions. Ectopic expression can be achieved in a number of ways including operably linking of a coding sequence encoding said protein to an isolated homologous or heterologous promoter in order to create a chimeric gene and/or operably linking said coding sequence to its own isolated promoter (i.e. the unisolated promoter naturally driving expression of said protein) in order to create a recombinant gene duplication or gene multiplication effect.

In the context of the present invention the term "modulating" relates to "enhancing or decreasing" the expression. According to at least one preferred embodiment of the invention, enhanced or increased expression of said nucleic acid is envisaged. Methods for obtaining enhanced or increased expression of genes or gene products are well documented in the art and can be for example couling to a strong constitutive promoter, or the use of transcription and/or translation enhancers. Methods for decreasing the expression and/o activity of a gene are for example the use of anti-sense, co-suppression, silencing, ribozymes, suppressors etc.

"Modulating the expression of the gene" also encompasses that transcriptlevel of the gene is altered and this can be the basis for the observed effects. For example, it is know that increasing the transcript level of a transgene in plants cannot only lead to increased protein levels, but alternatively, the transcripts can be involved in cosuppression of the native gene corresponding to the transgene.

The expression "expressible" relates to the presence of control sequences which promote adequate expression of genes and/or proper translation of said sequences into a specified protein. Said control sequences include promoter sequences which can be constitutive promoters or cell- or tissue-specific promoters. Also promoters are envisaged for use in the methods of the invention which are specific for dividing cells. In tables A and B, a non-exhaustive list of examples are given of such cell- and tissue-specific promoters, constitutive promoters and promoters specific for dividing cells.

Modulating, e.g. increasing or decreasing, the activity of a gene can be achieved for example by respectively inhibiting or stimulating the control elements that drive the expression of the native gene or of the transgene. Also modifying the activity of the gene product, the polypeptide, can furthermore be achieved by administering or exposing cells, tissues, organs or organisms to, an interacting protein or an inhibitor or activator of said gene product. In the context of the present invention, such inhibitors or activators can also affect their activity against the E2F protein or E2F/DP complex.

The expression "modulating the activity of an E2F transcription factor", for instance increasing the activity of the gene, the geneproduct, or the polypeptide encoded by the gene, can be achieved by administering or exposing cells, tissues, organs or organisms to, a preparation of said gene, gene product or said polypeptide, so that it can exert its functions in said exposed cells or tissues. In the context of the present invention, for instance the cells are exposed to protein samples of E2F protein or E2F/DP protein complexes.

It is demonstrated herein that the enlarged cotyledons of the arabidopsis plants transformed with E2F, contain smaller but 3 times as many cells compared to WT. The extra cells originate from additional cell divisions that occur after seed germination. Upon constitutive and ubiquitous overexpression of the E2Fa transcription factor, specific cells in the epidermis of the hypocotyl also show extra cell division but there is no difference in size of the hypocotyl between E2Fa transgenics and WT. Enhanced E2Fa levels therefore may prolong the period of cell division in certain cells and tissues such as cotyledons. The inventors have shown that E2Fa or E2F/DPa can sustain cell division in cells that are competent to divide. Except for the cotyledon size, the morphological characteristics of E2Fa transgenics are similar to WT plants. Also rice plants, transformed with the E2Fa gene and having more tillers and panicles, showed no deformations in the overall plant architecture.

Accordingly, an embodiment of the present invention is a method as described above for increasing the cell number of specific cell types, specific tissues or specific organs in a plant without altering the structure and/or composition of said specific cell, tissue or organ or whole plant Methods for monitoring the altered structure or composition of a tissue or organ or whole plant, are for example visual inspection of the external phenotypicand morphological characteristic such as overall shape of the tissue or organ or plant. For example, it can easily be seen if a leave is deformed or if the stem has an aberrant structure, or if the root has deformed structures. Also other techniques can be used to determine the morphological characteristics of a tissue such as the identity of the cells in the tissue or the organ or the plant, those techniques comprising microscopic analysis, histological assays, in situ hybridisation or in situ immunoprecipitation, FACS analysis, . . .

Overexpression of E2Fa leads to prolonging the period of cell division and/or other growth mechanisms together with harmonized increase of plant growth. This means that the balance between the basic cell cycle program and overall plant growth is not disturbed.

Accordingly, a particularly important technical feature of the present invention is that the overall architectural structure of the plant is not damaged. The radical change in cell faith and cell behavior, caused by overexpressing E2F, does not affect the overall tissue structure or composition of the plant. This feature of the present invention is extremely important, since altering a basic biological process may lead to deformation of the tissue. The delicacy of this balance is illustrated by the fact that overexpression of E2F together with its dimerization partner DP results in enhancing the effects seen when overexpressing E2F alone and leads to uncontrolled cell proliferation in differentiated tissue and consequently in the growth arrest early during the post-embryonic development of the plants.

The inventors showed that by introducing the E2Fa gene into a plant, they were able to enhance cell proliferation and to prolonge the period of cell division of certain cells in a certain organ of a plant. Surprisingly the inventors also found that general overexpression of E2F can be used to stimulate cells that are in the process of differentiation or differentiated cells to re-enter the cell cycle program. Although it was known that E2F plays a role in cell cycle control, it is now shown for the first time in plants, that cells, which do no longer divide spontaneously, (for example because they have differentiated), can now be influenced to re-enter the cell cycle again, by transforming them with E2Fa.

Therefore another embodiment of the present invention relates to a method to stimulate cells, to re-enter the cell cycle In a preferred embodiment cell types that are stimulated to re-enter cell cycle are cells in the process of differentiation or differentiated cells.

Re-entering the cell cycle means that the cells are normally not able to go into cell cycle since they have past that developmental stage and since they are destined to differentiate. The methods of the present invention can be used to alter that cell fate and to let such cells re-enter the cell cycle. This process takes more than just stimulating cell division, or stimulating cell cycle progression, since its needs to override the signals that determine the cells to differentiate and instead to force them to cross the first checkpoint of the cell cycle. The method of the present inventions is also no merely altering development since the overall development of the cell type or the tissue or the organ remains as it was: the structure and composition remain unaltered. Also, the method of the present invention is not merely altering differentiation i.e. reverse differentiation, because the effects of the method of the present invention are also on the level of well differentiated organs: for example very specifically the effects are in cotyledons, or tillers or panicles, which constitute differentiated tissue. Furthermore, the methods of the present invention are not merely altering growth, since growth is a process that does not necessarily means increasing the cell number. For instance growth can be mediated by faster growth or faster reaching the adult stage or increased size of the cells.

Also other preferred specific cell types to modify the expression or the activity of an E2F in, are meristematic cells, for example the shoot apical meristem or the root apical meristem.

The present inventors operationally linked the E2Fa transcription factor to several promoters and transformed these constructs into dicotyledonous or monocotyledonous plants. Surprisingly, in all cases the inventors observed an increase in cell number of particular cell types and/or an increase in size and/or in number of particular organs.

The present inventors surprisingly found that the constitutive and ubiquitous overexpression of the E2Fa transcription factor in Arabidopsis thaliana plants leads to enlarged cotyledons compared to wild-type (WT) plants. Furthermore, the seed preferred expression of this E2Fa gene in a rice plant resulted in rice plants with an increased number of tillers and panicles.

Therefore, according to a preferred embodiment the invention relates to any of the methods described herein for obtaining a plant with increased number of organs.

Alternatively, a preferred embodiment of the invention relates to any of the methods described herein for obtaining a plant with increased size of organs.

In a particular embodiment of the invention, said specific organ is a shoot, tiller, panicle, ear, flower, leave, cotyledon, stem, seed, root or tuber.

In a particular example of the invention, overexpression of E2F under control of a seed specific promoter leads to more seeds, and also to an increased size of the seeds. Biomass and yield are directly dependent on the number and size of organs, the architecture of the plant (number of branches), and seed mass production (storage accumulation dependent on photosynthetic assimilates). Therefore the method of the present invention can be used to increase the yield and therefore the economical importance of a plant, particularly monocots, graminea and cereals, are improved by using the methods of the present invention.

Depending on the promoter used (and of course the plant used, dicot versus monocot), the size and the number of different organs can be increased. The basic principle of this modification of the plant's architecture is the increase in cell number in particular tissues or organs. Surprisingly, the use of a constitutive promoter does not result in the increase in cell number in the whole plant since E2F works in a cell dependent way. Further, when E2F expression is limited to the seed, very surprisingly the number of tillers was increased as well as the number of panicles.

Accordingly, the present invention embodies a method to modify the yield of plants, such as cereals, graminae, crops or ornamentals. In a particular embodiment the methods of the present invention are used to modify corn by increasing the number of ears. Other particular embodiments of the invention comprise the methods as described above for application in grasses to increase in branch and/or tiller number, for instance to increase biomass production; for crops to increase number of tillers, panicles, flowers and seeds, for instance to increase total seed yield; for corn, late expression of the promoter is used to increase the number of branches in inflorescence meristems, leading to increased seed numbers; and for ornamentals to increase the branch number. The yield of said plants and the economical importance of said plants are significantly improved by the methods of the present invention.

A further embodiment of the invention relates to a method as mentioned above comprising stably integrating into the genome of said plant or in specific plant cells or tissues or organs of said plant an expressible nucleic acid encoding a plant E2F transcription factor, a homologue or a derivative thereof or an enzymatically active fragment thereof.

Another aspect of the invention relates to the complex between E2F2 transcription factors and their dimerisation partners. For instance the heterodimeric E2F/dimerization partner (DP) transcription factor regulates the promoter activity of multiple genes, which are essential for DNA replication and cell cycle control. One example of such a DP-like protein is isolated from Arabidopsis thaliana and its amino acid sequence is represented in SEQ ID NO 4. The corresponding nucleic acid sequence is represented in SEQ ID NO 3. The sequences are retrieved from the Genbank under the accession number AJ294531 (Magyar et al., 2000). The inventors surprisingly found that the effects of E2F could be enhanced by the co-expression of E2F together with DP.

The inventors showed for the fist time that ectopic expression of E2Fa/DPa early during development in differentiated cells results in cell proliferation. In contrast to the overexpression of other cell cycle genes that does not result in proliferation in differentiated tissue, surprisingly the overexpression of the E2F/DPa cell cycles genes can be used in plants to override the signals that regulate cell differentiation. In the case of general overexpression of E2Fa and DPa under the influence of a constitutive promoter, this method can be used as basis to create a growth arrest.

Accordingly a preferred embodiment is a method for enhancing cell proliferation in cells that are in the process of differentiation and for overriding the signals for differentiation in a plant comprising modulating the expression and/or activity in specific cells or tissues or organs of a plant E2F transcription factor and a plant E2F dimerization partner (DP), a homologue or a derivative thereof or an enzymatically active fragment thereof.

"Enhancing cell proliferation in differentiated cells" means that the cell division in differentiated cells is stimulated in such a way that the continuous cell division results in an excess of cell number. Proliferation does not normally occur in differentiated tissues, since the cells in that tissue are programmed to stop dividing.

"Overriding the signals for differentiation in a plant" means that the cell fate is altered. Normally differentiated cells are programmed to stop dividing and this programming occurs via certain signal transduction pathways. Overriding the signals for differentiation means that the process of differentiation is hindered to be completed.

A further embodiment of the invention relates to a method as described above comprising stably integrating into the genome of said plant or in specific plant cells or tissues or organs of said plant an expressible nucleic acid encoding a plant E2F transcription factor and least one expressible nucleic acid encoding a plant E2F dimerization partner (DP), a homologue or a derivative thereof or an enzymatically active fragment thereof.

Plant E2F transcription factors have been isolated and sequenced and are known in the art. One exemplary nucleic acid encoding an E2F transcription factor is represented in SEQ ID NO 1 and its corresponding amino acid sequence is represented in SEQ ID NO 2. These sequences are deposited in the Genbank database under the accession number AJ294534 and relates to *Arabidopsis thaliana* mRNA encoding an E2F-related protein (E2Fa gene) (Magyar et al., 2000). This gene, Arath;E2Fa can also be found in the public databases under the MIPS accession number At2g36010 F11F19.8 and corresponds to the protein CAC15486. A splice variant of the *Arabidopsis thaliana* E2Fa transcription factor is represented in SEQ ID NO 19, encoding a polypeptide as represented in SEQ ID NO 20. This sequence was isolated for the first time by the inventors and showed to have one amino acid substitution compared with the E2F factor according the sequence SEQ ID NO 2 or CAC15486.

It should be clear that the invention is not be limited to said nucleic acid and/or said proteins but also other known E2F transcription factors are useful in the methods of the present invention. It is clear that many allelic variants or splice variants of the E2Fa factor exist and these variants can also be used in the methods of the present invention. Also homologues of E2Fa in other plant species can be identified, for example by screening the sequence databases with the Arath; E2Fa sequence and designing degenerative primers for using in a PCR reaction on a cDNA library of another organism; and these homologues can also be used in the methods of the present invention. Also Arath;E2Fb (MIPS accession number At5g22220 T6G21.10 and corresponding to the protein CAC15485) is a gene that is also particularly interesting to use in the methods of the present invention, since E2Fa and E2Fb be are closely related. Also Arath;E2Fc (MIPS accession number At1g47870 T2T6.2 and corresponding to the protein CAD10631) and homologues E2F factors of other plant species are known in the art and can be used for the methods of the present invention.

According to a specific embodiment the present invention relates to any method of the present invention, wherein said E2F transcription factor is E2Fa, for example, but not limited to E2Fa from *Arabidopsis thaliana*.

Accordingly, the present invention also embodies any of the methods as described in the present invention, wherein the E2F transcription factor is selected from the group consisting of E2F, preferably E2Fa from Arabidopsis thaliana, or E2Fb or E2Fc and wherein the DP is selected from the group consisting of DPa, preferably DPa from *Arabidopsis thaliana* and DPb.

Further, the inventors surprisingly found that in monocotyledonous plants, such as rice, the number of tillers and/or the numbers of panicles were increased, when the E2F transcription factor was overexpressed and when said overexpression of E2F was specifically in the seed of said plants.

In a preferred embodiment said plant is a monocotyledonous plant, such as rice, and said E2F transcription factor is the AtE2Fa transcription factor, as set forth in SEQ ID NO 1, or in as set forth in SEQ ID NO 19, which is a splice variant of AtE2Fa.

Preferably, said method comprising stably integrating into the genome of said plant or in specific plant cells or tissues of said plant an expressible nucleic acid encoding a plant E2F transcription factor, a homologue or a derivative thereof or an enzymatically active fragment thereof. In a preferred embodiment the E2F factor, such as a E2Fa factor, is under the control of a seed specific promoter, such as the rice oleosin promoter.

Accordingly, another embodiment is any method as described in the present invention wherein the nucleic acid encoding a plant E2F transcription factor is represented by SEQ ID NO 2 or 20, or a homologue or a derivative thereof or an enzymatically active fragment thereof.

Also, the invention relates to a method comprising enhancing the expression or activity in specific cells or tissues of a plant E2F transcription factor, a homologue or a derivative thereof or an enzymatically active fragment thereof for instance by enhancing the expression of a nucleic acid encoding a plant E2F transcription factor, a homologue or a derivative thereof or an enzymatically active fragment thereof in said specific cells or tissues. Said enhancement of the expression of the gene is mediated by overexprssion of that gene.

Accordingly, the present invention embodies any of the methods as herein described, comprising overexpression of a nucleic acid encoding said plant E2F transcription factor.

A further embodiment of the invention relates to any of the methods as herein described for the production of a transgenic plant, comprising the steps of (a) providing or making a DNA construct comprising a regulatory sequence, that is capable of modifying the expression and/or activity of an E2F transcription factor, and operably linking this regulatory sequence to a gene encoding an E2F transcription factor,
(b) transforming said DNA construct in a plant cell,
(c) cultivating the transgenic cell obtained from step (b) under conditions promoting regeneration and mature plant growth, (d) selecting and evaluating said plant during the course of development to registrate its phenotypic and morphological characteristics.

In a preferred embodiment said regulatory sequence is a promoter. Alternatively, said regulatory sequence is not operably linked to the E2F gene in said DNA construct, but the regulatory sequence is used to influence the expression of the native E2F gene in the host cell.

In preferred embodiment said regulatory sequence is chose n from the group consisting of a promoter, an enhancer, a transcription enhancer, a translation and enhancer.

Further, the present invention relates to any of the methods herein described wherein said E2F is under the control of a seed specific, and/or embryo specific promoter, such as the oleosin promoter The LEAFY promoter is also used to express the E2F gene in rice and corn during induction of flower formation. This strategy allows obtaining plants with increased number of cell production during flower formation, i.e. increased number of cells in the inflorescence meristem, and therefore increased number and/or size of seeds.

The CDC2a promoter is used to drive expression E2Fa and leads to plants having increased number of cells in shoot apical meristem (SAM) and root apical meristem (RAM). This vegetative meristem is first transformed into an inflorescence meristem, which than generates the floral meristem. As a consequence more and/or larger organs can be formed from this meristems. The MCM3 promoter (Stevens et al., 2002) or RNR promoter (Chaboute et al. 2002) which are expressed in actively dividing zones is also used in the methods of the present invention to increase the number of cells in the meristems.

The plant cells or plants used in the methods of the present invention include all plants or cells of plants which belong to the superfamily *Viridiplantae*, including both monocotyledonous and dicotyledonous plants. Two of the most preferred plants for use in the methods of the invention are *Arabidopsis thaliana* and *Oryza sativa* (rice).

According to another embodiment, the present invention further relates to any of the methods herein described wherein said plant or plant cell is derived from rice (*Oryza sativa*).

The invention further relates to all transgenic plants obtainable by any of the methods of the invention showing for example stimulated cell division in specific cells or cell tissues. Preferably, the invention relates to a transgenic plant having altered expression and/or activity of an E2F transcription factor and having more cells in a particular plant tissue or organ, and/or enlarged organs such as enlarged cotyledons and/or enlarged tillers and/or enlarged panicles and/or enlarged shoots and/or enlarged flowers and/or enlarged roots and/or enlarged seeds and/or enlarged tubers .

Further, the invention relates to a transgenic plant having altered expression and/or activity of an E2F transcription factor and having more cells in a particular plant tissue or organ, and/or more organs such as more tillers and/or more panicles and/or more shoots and/or more flowers and/or more roots and/or more seeds and/or more tubers.

Accordingly, the invention also embodies a transgenic plant obtainable by any of the methods as described above.

Also a particular embodiment of the invention relates to a part, particularly a harvestable part of a transgenic plant as described above Modulating, e.g. lowering or augmenting, the level of active gene products or of gene product activity can furthermore be achieved by administering or exposing cells, tissues, organs or organisms to, respectively, an inhibitor or activator of said gene product. In the context of the present invention, such inhibitors or activators can also effect their activity against the E2F protein or E2F/DP complex. Such inhibitors or activators include proteins and chemical compounds which are obtainable and/or identified for instance by one of the following methods.

Accordingly, another embodiment of the present invention is a method for identifying and obtaining compounds that interfere with the interaction between an E2F transcription factor and its dimerization partner comprising the steps of:

a) providing a two-hybrid system wherein a nucleic acid encoding an E2F transcription factor represented by SEQ ID NO 2 or 20 or a homologue or a derivative thereof or an enzymatically active fragment thereof and its dimerisation partner represented by SEQ ID NO 4, or a homologue or a derivative thereof or an enzymatically active fragment thereof are expressed, b) interacting at least one compound with the complex formed by the expressed polypeptides as defined in (a), and, c) measuring the effect of said compound on the binding between the interacting proteins as defined in (a) or measuring the activity of said complex, d) optionally identifying said compound.

The invention further relates to the above described methods wherein said compound enhances the activity of said protein complex or promotes the formation of a complex between said proteins. The invention further relates to the compounds obtainable by said methods.

According to another embodiment the present invention relates to a compound identified or identifiable by means of the above methods as a plant growth regulator. The invention also relates to a method for producing a plant growth regulator comprising the steps of the above methods and formulating the compounds obtained from said steps in a suitable form for the application in agriculture or plant cell or tissue culture.

The invention further relates to different new uses of E2F transcription factors. The E2F factor used in the present invention can be any E2F factor chosen from the group of E2Fa, E2Fb and E2Fc. Also the E2F factor to be used in the present invention can be used alone or in combination with its dimerization partner DP. This DP is any DP or a DP chosen from the group consisting of DPa and DPb. In a particular example of the present invention an E2Fa transcription factor from *Arabidopsis* thaliana is used or a E2Fa factor, represented by the sequences of SEQ ID NOs 1, 2, 19 and 20. In a particular example of the invention the DPa factor of *Arabdopsis thaliana* is used or the DP factor as represented in SEQ ID NO 3 and 4.

In a preferred embodiment of the present invention the uses of the E2F or DP factor comprise modulating the expression and/or activity in specific cells or tissues or organs of a plant E2F transcription factor and a plant E2F dimerization partner (DP), a homologue or a derivative thereof or an enzymatically active fragment thereof, for instance by enhancing the expression of a nucleic acid encoding a plant E2F transcription factor alone or in combination with a nucleic acid encoding a plant DP, or a homologue or a derivative of said nucleic acids or an enzymatically active fragment thereof, in said specific cells or tissues.

In a particular embodiment of the invention the uses of E2F or DP involve stably integrating into the genome of said plant or in specific plant cells or tissues of said plant an expressible nucleic acid encoding a plant E2F transcription factor or an expressible nucleic acid encoding a plant E2F dimerization partner (DP), a homologue or a derivative thereof or an enzymatically active fragment thereof.

Therefore, another embodiment of the present invention relates to the use of an E2F transcription factor, or a homologue or a derivative thereof or an enzymatically active fragment thereof for prolonging the period of cell division in certain cells and tissues.

The expression "prolonging the period of cell division" means altering the fate of cells that are dividing in such a way that they do not stop dividing, but instead continue to divide. The expression means that the cells of the present invention have a prolonged period of cell division compared to cells wherein the expression and/or activity of E2F is not modulated. Prolonged period of cell division can be observed by visual inspection f the tissue to see if there are more cells and/or if the organ is bigger, or by microscopic analysis or histological assays.

Further the present invention relates to the use of an E2F transcription factor, or a homologue or a derivative thereof or an enzymatically active fragment thereof for increasing the size of cotyledons.

Enlarged cotyledons in said transgenic plants results in enhanced vigor of the seedlings, which could translate in a faster growth rate (e.g. better growth at the juvenile stage resulting in an overall faster growth at the adult stage), higher stress resistance, and better survival of seedlings.

Accordingly, the present invention relates to the use of an E2F transcription factor, or a homologue or a derivative thereof or an enzymatically active fragment thereof for enhancing cell proliferation after seed germination.

Further the present invention relates to the use of an E2F transcription factor, or a homologue or a derivative thereof or an enzymatically active fragment thereof for enhancing the stress resistance of seedlings.

Further the present invention relates to the use of an E2F transcription factor, or a homologue or a derivative thereof or an enzymatically active fragment thereof for obtaining seedlings with enhanced vigor. Further the present invention relates to the use of an E2F transcription factor, or a homologue or a derivative thereof or an enzymatically active fragment thereof for obtaining plants that have increased growth.

Further the present invention relates to the use of an E2F transcription factor, or a homologue or a derivative thereof or an enzymatically active fragment thereof for obtaining plants having more cells in a particular tissue The expression "more cells" relates to a plant having more cells in the same tissue or organ when compared with the tissue or organ of another plant (of same species, same age, in same environments) wherein of expression and/or activity of an E2F transcription factor is not modulated.

More cells in said transgenic plants can be used to alter architectural features, for example to alter wood structure, for example to make it more dense and heavier. These altered features can have a beneficial effect for example on the pathogen resistance of the plant and the quality of the plant material. Therefore the methods of the present invention can significantly contribute to the industrial applicability of said transgenic plants. More cells in said transgenic plants could also be used for altering biochemical features of the plant for example to produce more cell wall components. Examples of industrial application of these plants are the cultivation of the plants for the production of lignin, cellulose, pectin etc.

Further the present invention relates to the use of an E2F transcription factor, or a homologue or a derivative thereof or an enzymatically active fragment thereof for obtaining plants having an increased number of organs.

Further the present invention relates to the use of an E2F transcription factor, or a homologue or a derivative thereof or an enzymatically active fragment thereof for obtaining plants having an increased size of organs.

Further the present invention relates to the use of an E2F transcription factor, or a homologue or a derivative thereof or an enzymatically active fragment thereof for obtaining plants having an increased yield Further the present invention relates to the use of an E2F transcription factor, or a homologue or a derivative thereof or an enzymatically active fragment thereof for stimulating differentiated cells to re-enter the cell cycle.

Further the present invention relates to the use of an E2F transcription factor, or a homologue or a derivative thereof or an enzymatically active fragment thereof for overriding the cell differentiation signals.

The inventors also showed that overexpression of E2F and DP results in altered cell shape in some cells or some tissues of the plant. Therefore the present invention relates to the use of an E2F transcription factor, or a homologue or a derivative thereof or an enzymatically active fragment thereof for altering cell shape.

Definitions and Elaborations to the Embodiments

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any or more of said steps or features.

Nucleic acids are written left to right in 5' to 3' orientation, unless otherwise indicated; amino acid sequences are written left to right in amino to carboxy orientation. Amino acids may be referred to herein by either their commonly known three letter symbols or by the one-letter symbols recommended by the IUPAC-IUB Biochemical Nomenclature Commission. Nucleotides may be referred to by their commonly accepted single-letter codes.

The terms "gene(s)", "polynucleotide(s)", "nucleic acid(s)", "nucleotide sequence(s)", "nucleic acid sequence(s)", or 'nucleic acid molecule(s)' as used herein refer to a polymeric form of a deoxyribonucleotides or ribonucleotide polymer of any length, either double- or single-stranded, or analogs thereof, that have the essential characteristic of a natural ribonucleotide in that they can hybridize to nucleic acids in a manner similar to naturally occurring polynucleotides.

A great variety of modifications have been made to DNA and RNA that serve many useful purposes known to those skilled in the art. For example, methylation, 'caps' and substitution of one or more of the naturally occurring nucleotides with an analog. Said terms also include peptide nucleic acids.

The term "polynucleotide" as used herein includes such chemically, enzymatically or metabolically modified forms of polynucleotides.

"Sense strand" refers to a DNA strand that is homologous to a mRNA transcript thereof, "antisense strand" refers to the complementary strand of the sense strand.

By "encoding" or "encodes" with respect to a specified nucleotide sequence is meant comprising the information for translation into a specified protein. A nucleic acid encoding a protein may contain non-translated sequences such as 5' and 3' untranslated regions (5' and 3' UTR) and introns or it may lack intron sequences such as for example in cDNAs.

An "open reading frame" or "(ORF)" is defined as a nucleotide sequence that encodes a polypeptide. The information by which a protein is encoded is specified by the use of codons. Typically, the amino acid sequence is encoded by the nucleic acid using the 'universal'0 genetic code but variants of this universal code exist (see for example Proc. Natl. Acad. Sci. U.S.A 82: 2306-2309 (1985)). The boundaries of the coding sequence are determined by a translation start codon at the 5'-end and a translation stop codon at the 3'-terminus.

As used herein "full-length sequence" with respect to a specific nucleic acid or its encoded protein means having the entire amino acid sequence of a native protein. In the present invention, comparison to known full-length homologous (orthologous or paralogous) sequences is used to identify full-length sequences. Also, for a mRNA or cDNA, consensus sequences present at the 5' and 3' untranslated regions aid in the identification of a polynucleotide as full-length. For a protein, the presence of a start- and stop-codon aid in identifying the polypeptide as full-length. When the nucleic acid is to be expressed, advantage can be taken of known codon preferences or GC content preferences of the intended host as these preferences have been shown to differ (see e.g. http://www.kazusa.or.jp/codon/; Murray et al., Nucl. Acids Res. 17: 477-498 (1989)). Because of the degeneracy of the genetic code, a large number of nucleic acids can encode any given protein. As such, substantially divergent nucleic acid sequences can be designed to effect expression of essentially the same protein in different hosts. Conversely, genes and coding sequences essentially encoding the same protein isolated from different sources can consist of substantially different nucleic acid sequences.

An "expressible nucleic acid" as used herein means a ucleic acid that carries the necessary control elements to be effective in the host cell.

The term "control sequence" or "regulatory sequence" or "regulatory element" refers to regulatory nucleic acid sequences which are necessary to effect the expression of sequences to which they are ligated. The control sequences differ depending upon the intended host organism and upon the nature of the sequence to be expressed. For expression of a protein, in prokaryotes, the control sequences generally include a promoter, a ribosomal binding site, and a terminator. In eukaryotes, control sequences generally include promoters, terminators and, in some instances, enhancers, and/or 5' and 3' untranslated sequences. The term "control sequence" is intended to include, at a minimum, all components necessary for expression, and may also include additional advantageous components.

As used herein, a "promoter" includes reference to a region of DNA upstream from the transcription start and involved in binding RNA polymerase and other proteins to start transcription. Reference herein to a 'promoter' is to be taken in its broadest context and includes the transcriptional regulatory sequences derived from a classical eukaryotic genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner. The term "promoter" also includes the transcriptional regulatory sequences of a classical prokaryotic gene, in which case it may include a −35 box sequence and/or a −10 box transcriptional regulatory sequences. The term "promoter" is also used to describe a synthetic or fusion molecule, or derivative which confers, activates or enhances expression of a nucleic acid molecule in a cell, tissue or organ.

A "plant promoter" is a promoter capable of initiating transcription in plant cells.

"Tissue-preferred" promoters as used herein refers to promoters that preferentially initiate transcription in certain tissues such as for example in leaves, roots, etc. Promoters which initiate transcription only in certain tissues are referred herein as 'tissue-specific'. Examples of plant tissue-specific or tissue-preferred promoters are given in Table A.

Those skilled in the art will be aware that "inducible promoters" have induced or increased transcription initiation in response to a developmental, chemical, environmental, or physical stimulus.

A "constitutive promoter" is transcriptionally active during most, but not necessarily all phases of its growth and development. Examples of constitutive plant promoters are given in Table B.

The term "terminator" as used herein is an example of a "control sequence" and refers to a DNA sequence at the end of a transcriptional unit which signals 3' processing and polyadenylation of a primary transcript and termination of transcription. Terminators comprise 3'-untranslated sequences with polyadenylation signals, which facilitate 3' processing and the addition of polyadenylated sequences to the 3'-end of a primary transcript. Terminators active in cells derived from viruses, yeasts, moulds, bacteria, insects, birds, mammals and plants are known and described in the literature. They may be isolated from bacteria, fungi, viruses, animals and/or plants. Additional regulatory elements may include transcriptional as well as translational enhancers. A plant translational enhancer often used is the CaMV omega sequences. The inclusion of an intron has been shown to increase expression levels by up to 100-fold in certain plants (Mait, Transgenic Research 6 (1997), 143-156; Ni, Plant Journal 7 (1995), 661-676).

TABLE A

Exemplary plant tissue-specific or tissue-preferred promoters

| GENE SOURCE | EXPRESSION PATTERN | REFERENCE |
|---|---|---|
| α-amylase (Amy32b) | Aleurone | Lanahan, MB, et al., Plant Cell 4: 203-211, 1992; Skriver, K, et al., Proc. Natl. Acad. Sci. (USA) 88: 7266-7270, 1991. |
| Cathepsin β-like gene | Aleurone | Cejudo, FJ, et al., Plant Mol. Biol. 20: 849-856, 1992. |
| *Agrobacterium rhizogenes* rolB | Cambium | Nilsson et al., Physiol. Plant. 100: 456-462, 1997. |
| PRP genes | cell wall | http://salus.medium.edu/mmg/tierney/html |
| Chalcone synthase (chsA) | Flowers | Van der Meer et al., Plant Mol. Biol. 15: 95-109, 1990. |
| LAT52 | Anther | Twell et al., Mol. Gen. Genet. 217: 240-245, 1989. |
| Apetala-3 | Flowers | |
| *Chitinase* | fruit (berries, grapes, etc) | Thomas et al., CSIRO Plant Industry, Urrbrae, South Australia, Australia; http://winetitles.com.au/gwrdc/csh95-1.html |
| Rbcs-3A | green tissue (eg leaf) | Lam et al., The Plant Cell 2: 857-866, 1990; Tucker et al., Plant Physiol. 113: 1303-1308, 1992. |
| Leaf-specific genes | Leaf | Baszczynski et al., Nucl. Acids Res. 16: 4732, 1988. |
| Chlorella virus adenine methyl-transferase gene promoter | Leaf | Mitra and Higgins, Plant Mol. Biol. 26: 85-93, 1994. |

TABLE A-continued

Exemplary plant tissue-specific or tissue-preferred promoters

| GENE SOURCE | EXPRESSION PATTERN | REFERENCE |
|---|---|---|
| AldP gene promoter from rice | Leaf | Kagaya et al., Mol. and Gen. Genet. 248: 668-674, 1995. |
| Rbcs promoter from rice or tomato | Leaf | Kyozuka et al., Plant Physiol. 102: 991-1000, 1993. |
| Pinus cab-6 | Leaf | Yamamoto et al., Plant Cell Physiol. 35: 773-778, 1994. |
| Rubisco promoter | Leaf | |
| Cab (chlorophyll a/b binding protein) | Leaf | |
| SAM22 | senescent leaf | Crowell et al., Plant Mol. Biol. 18: 459-466, 1992. |
| Ltp gene (lipid transfer gene) | | Fleming et al., Plant J. 2: 855-862, |
| *R. japonicum* nif gene | Nodule | U.S. Pat. No. 4,803,165 |
| *B. japonicum* nifH gene | Nodule | U.S. Pat. No. 5,008,194 |
| GmENOD40 | Nodule | Yang et al., The Plant J. 3: 573-585, |
| PEP carboxylase (PEPC) | Nodule | Pathirana et al., Plant Mol. Biol. 20: 437-450, 1992. |
| Leghaemoglobin (Lb) | Nodule | Gordon et al., J. Exp. Bot. 44: 1453-1465, 1993. |
| *Tungro bacilliform* virus gene | Phloem | Bhattacharyya-Pakrasi et al., The Plant J. 4: 71-79, 1992. |
| Sucrose-binding protein gene | plasma membrane | Grimes et al., The Plant Cell 4: 1561-1574, 1992. |
| Pollen-specific genes | pollen; microspore | Albani et al., Plant Mol. Biol. 15: 605, 1990; Albani et al., Plant Mol. Biol. 16: 501, 1991. |
| Zm13 | Pollen | Guerrero et al., Mol. Gen. Genet. 224: 161-168, 1993. |
| Apg gene | Microspore | Twell et al., Sex. Plant Reprod. 6: 217-224, 1993. |
| Maize pollen-specific gene | Pollen | Hamilton et al., Plant Mol. Biol. 18: 211-218, 1992. |
| Sunflower pollen-expressed gene | Pollen | Baltz et al., The Plant J. 2: 713-721, 1992. |
| *B. napus* pollen-specific gene | pollen;anther; tapetum | Arnoldo et al., J. Cell. Biochem., Abstract No. Y101, 204, 1992. |
| Root-expressible genes | Roots | Tingey et al., EMBO J. 6: 1, 1987. |
| Tobacco auxin-inducible gene | Root tip | Van der Zaal et al., Plant Mol. Biol. 16, 983, 1991. |
| β-tubulin | Root | Oppenheimer et al., Gene 63: 87, 1988. |
| Tobacco root-specific genes | Root | Conkling et al., Plant Physiol. 93: 1203, 1990. |
| *B. napus* G1-3b gene | Root | U.S. Pat. No. 5,401,836 |
| SbPRP1 | Roots | Suzuki et al., Plant Mol. Biol. 21: 109-119, 1993. |
| AtPRP1; AtPRP3 | Roots; root hairs | http://salus.medium.edu/mmg/tierney/html |
| RD2 gene | root cortex | http://www2.cnsu.edu/ncsu/research |
| TobRB7 gene | root vasculature | http://www2.cnsu.edu/ncsu/research |
| AtPRP4 | Leaves; flowers; lateral root primordia | http://salus.medium.edu/mmg/tierney/html |
| Seed-specific genes | Seed | Simon et al., Plant Mol. Biol. 5: 191, 1985; Scofield et al., J. Biol. Chem. 262: 12202, 1987; Baszczynski et al., Plant Mol. Biol. 14: 633, 1990. |
| Brazil Nut albumin | Seed | Pearson et al., Plant Mol. Biol. 18: 235-245, 1992. |
| Legumin | Seed | Ellis et al., Plant Mol. Biol. 10: 203-214, 1988. |

TABLE A-continued

Exemplary plant tissue-specific or tissue-preferred promoters

| GENE SOURCE | EXPRESSION PATTERN | REFERENCE |
|---|---|---|
| Glutelin (rice) | Seed | Takaiwa et al., Mol. Gen. Genet. 208: 15-22, 1986; Takaiwa et al., FEBS Letts. 221: 43-47, 1987. |
| Zein | Seed | Matzke et al., Plant Mol. Biol., 14: 323-332, 1990. |
| NapA | Seed | Stalberg et al., Planta 199: 515-519, 1996. |
| Wheat LMW and HMW glutenin-1 | Endosperm | Mol Gen Genet 216: 81-90, 1989; NAR 17: 461-462, 1989 |
| Wheat SPA | Seed | Albani et al, Plant Cell, 9: 171-184, 1997. |
| Wheat α,β,γ-gliadins | Endosperm | EMBO 3: 1409-15, 1984 |
| Barley Itr1 promoter | Endosperm | |
| Barley B1, C, D, hordein | Endosperm | Theor Appl Gen 98: 1253-1262, 1999; The Plant J. 4: 343-355, 1993; Mol Gen Genet 250: 750-760, 1996. |
| Barley DOF | Endosperm | Mena et al., The Plant J. 116: 53-62, 1998. |
| Blz2 | Endosperm | EP99106056.7 |
| Synthetic promoter | Endosperm | Vicente-Carbajosa et al., The Plant J. 13: 629-640, 1998. |
| Rice prolamin NRP33 | Endosperm | Wu et al., Plant Cell Physiol. 39: 885-889, 1998 |
| Rice α-globulin Glb-1 | Endosperm | Wu et al., Plant Cell Physiol. 39: 885-889, 1998 |
| Rice OSH1 | Embryo | Sato et al., Proc. Natl. Acad. Sci. USA, 93: 8117-8122, 1996. |
| Rice α-globulin REB/OHP-1 | Endosperm | Nakase et al., Plant Mol. Biol. 33: 513-522, 1997. |
| Rice ADP-glucose PP | Endosperm | Trans. Res. 6: 157-168, 1997. |
| Maize ESR gene family | Endosperm | The Plant J. 12: 235-246, 1997. |
| Sorghum γ-kafirin | Endosperm | DeRose RT et al., Plant Mol. Biol. 32: 1029-1035, 1996. |
| KNOX | Embryo | Postma-Haarsma et al., Plant Mol. Biol. 39: 257-271, 1999. |
| Rice oleosin | Embryo and aleuron | Wu et el., J. Biochem., 123: 386, 1998. |
| Sunflower oleosin | seed (embryo and dry seed) | Cummins et al., Plant Mol. Biol. 19: 873-876, 1992. |
| LEAFY | shoot meristem | Weigel et al., Cell 69: 843-859, 1992. |
| *Arabidopsis thaliana* knat1 | shoot meristem | Accession number AJ131822 |
| *Malus domestica* kn1 | shoot meristem | Accession number Z71981 |
| CLAVATA1 | shoot meristem | Accession number AF049870 |
| Stigma-specific genes | Stigma | Nasrallah et al., Proc. Natl. Acad. Sci. USA 85: 5551, 1988; Trick et al., Plant Mol. Biol. 15: 203, 1990. |
| Class I patatin gene | Tuber | Liu et al., Plant Mol. Biol. 153: 386-395, 1991. |
| PCNA rice | Meristem | Kosugi et al., Nucl. Acids Res. 19: 1571-1576, 1991; Kosugi S. and Ohashi Y, Plant Cell 9: 1607-1619, 1997. |
| Pea TubA1 tubulin | Dividing cells | Stotz and Long, Plant Mol. Biol. 41: 601-614, 1999. |
| *Arabidopsis* cdc2a | cycling cells | Chung and Parish, FEBS Lett, 362: 215-219, 1995. |
| *Arabidopsis* Rop1A | Anthers; mature pollen + pollen tubes | Li et al., Plant Physiol.118: 407-417, 1998. |
| *Arabidopsis* AtDMC1 | Meiosis-associated | Klimyuk and Jones, The Plant J. 11: 1-14, 1997. |
| Pea PS-IAA4/5 and PS-IAA6 | Auxin-inducible | Wong et al., Plant J. 9: 587-599, 1996. |

TABLE A-continued

Exemplary plant tissue-specific or tissue-preferred promoters

| GENE SOURCE | EXPRESSION PATTERN | REFERENCE |
| --- | --- | --- |
| Pea farnesyltransferase | Meristematic tissues; phloem near growing tissues; light-and sugar-repressed | Zhou et al., Plant J. 12: 921-930, 1997. |
| Tobacco (*N. sylvestris*) cyclin B1; 1 | Dividing cells/ meristematic tissue | Trehin et al., Plant Mol. Biol. 35: 667-672, 1997. |
| *Catharanthus roseus* Mitotic cyclins CYS (A-type) and CYM (B-type) | Dividing cells/ meristematic tissue | Ito et al., The Plant J. 11: 983-992, 1997. |
| *Arabidopsis* cyc1At (=cyc B1; 1) and cyc3aAt (A-type) | Dividing cells/ meristematic tissue | Shaul et al., Proc. Natl. Acad. Sci. U.S.A 93: 4868-4872, 1996. |
| *Arabidopsis* tef1 promoter box | Dividing cells/ meristematic tissue | Regad et al., Mol. Gen. Genet. 248: 703-711, 1995. |
| *Catharanthus roseus* cyc07 | Dividing cells/ meristematic tissue | Ito et al., Plant Mol. Biol. 24: 863-878, 1994. |

TABLE B

Exemplary constitutive plant promoters for use in the performance of the current invention.

| GENE SOURCE | REFERENCE |
| --- | --- |
| Actin | McElroy et al., Plant Cell 2: 163-171, 1990. |
| CAMV 35S | Odell et al., Nature 313: 810-812, 1985. |
| CaMV 19S | Nilsson et al., Physiol. Plant. 100: 456-462, 1997. |
| GOS2 | de Pater et al., The Plant J. 2: 837-44, 1992. |
| Ubiquitin | Christensen et al., Plant Mol. Biol. 18: 675-689, 1992. |
| Rice cyclophilin | Buchholz et al., Plant Mol Biol. 25: 837-43, 1994. |
| Maize H3 histone | Lepetit et al., Mol. Gen. Genet. 231: 276-285, 1992. |
| Actin 2 | An et al., The Plant J. 10: 107-121, 1996. |

The term "operably linked" as used herein refers to a juxtaposition wherein the components so described are in a relationship permitting them to function in their intended manner. A control sequence 'operably linked' to a coding sequence is ligated in such a way that expression of the coding sequence is achieved under conditions compatible with the control sequences. In case the control sequence is a promoter, it is obvious for a skilled person that double-stranded nucleic acid is used.

The term 'hybridizing' includes reference to formation of a duplex nucleic acid structure through annealing of two single-stranded nucleic acid sequences. The hybridization process can occur entirely in solution like for example in the polymerase chain reaction process, subtractive hybridization, and cDNA synthesis. Alternatively, one of the complementary nucleic acids can be immobilized on a solid support such as on a nylon membrane in DNA and RNA gel blot analyses or on a siliceous glass support for microarray hybridization. Other uses and techniques relying on hybridization are well known to those skilled in the art. The critical factors for hybridization are the ionic strength and temperature of the solution and characteristics of the nucleic acids such as length and % GC content. The $T_m$ is the temperature at which 50% of a complementary target sequence hybridizes to a perfectly matched probe under defined ionic strength and pH. For DNA-DNA hybrids, the $T_m$ can be calculated from the equation of Meinkoth and Wahl (Anal. Biochem., 138: 267-284, 1984): $T_m$=81.5° C.+16.6 (logM)+0.41 (% GC)−0.61 (% formamide)−500/L where M is the molarity of monovalent cations, % GC is the percentage of guanosine and cytosine nucleotides in the DNA, % formamide is the percentage of formamide in the hybridization solution, and L is the length of the hybrid in base pairs.

The terms 'stringent conditions' or 'stringent hybridization conditions' includes reference to conditions under which a probe will hybridize to its target sequence to a detectable greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe. Alternatively, stringency conditions can be adjusted to allow some mismatching so that sequences with lower degrees of similarity are detected. Stringent conditions are those in which the salt concentration is less than about 1.5M Na ion, typically 0.01 to 1.0 M Na ion (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. An example of low stringency conditions includes hybridization with a buffer solution of 30 to 35% formamide, 1M NaCl, 1% SDS (sodium dodecyl sulfate) at 37° C., and a wash in 1× to 2×SSC (20×SSC is 3.0 M NaCl/0.3M trisodium citrate) at 50 to 55° C. Exemplary moderate stringency conditions include hybridization in 40 to 45% formamide, 1M NaCl, 1% SDS at 37 C, ands a wash in 0.5×SSC to 1.0×SSC at 55 to 60° C. Exemplary high stringency conditions include hybridization in 50% formamide, 1M NaCl, 1% SDS at 37° C., and a wash in 0.1×SSC at 60 to ° 65C. Specificity is typically the function of post—hybridization washes. Those skilled in the art will understand that the conditions for hybridization and washing can be adjusted to achieve hybridization to sequences of the desired identity. A guide to the hybridization of nucleic acids is found in Sambrook, Molecular Cloning; A Laboratory Manual, 2nd Edition, Cold Spring Harbor Laboratory Press, Cold Spring Harbor, N.Y. (1989); and in Tijssen, Laboratory Techniques in Biochemistry and Molecular Biology-Hybridization with Nucleic Acid Probes, Part I, Chapter 2 'Overview of principles of hybridization and the strategy of nucleic acid probe assays', Elsevier, New York (1993).

The terms "protein" and "polypeptide" are interchangeable used in this application and refer to a polymer of amino acids. These terms do not refer to a specific length of the molecule and thus peptides and oligopeptides are included within the definition of polypeptide. This term also refers to or includes post-translational modifications of the polypeptide, for example, glycosylations, acetylations, phosphorylations, sulfations and the like. These modifications are well known to those skilled in the art and examples are described by Wold F., Posttranslational Protein Modifications: Perspectives and Prospects, pp. 1-12 in Posttranslational Covalent Modification of Proteins, B. C. Johnson, Ed., Academic Press, New York (1983) and Seifter et al., Meth. Enzymol. 182: 626-646 (1990). Included within the definition are, for example, polypeptides containing one or more analogues of an amino acid (including, for example, unnatural amino acids, etc.), polypeptides with substituted linkages, as well as other naturally and non-naturally occurring modifications known in the art.

The term "amino acid", "amino acid residue" or "residue" are used interchangeably herein to refer to an amino acid that is incorporated into a protein, polypeptide, or peptide. The amino acid may be a naturally occurring amino acid and may be a known analogue of natural amino acids that can function in a similar manner as naturally occurring amino acids.

As used herein "homologues" of a protein of the invention are those peptides, oligopeptides, polypeptides, proteins and enzymes which contain amino acid substitutions, deletions and/or additions relative to said protein, providing similar biological activity as the unmodified polypeptide from which they are derived. To produce such homologues, amino acids present in the said protein can be replaced by other amino acids having similar properties, for example hydrophobicity, hydrophilicity, antigenicity, propensity to form or break α-helical structures or β-sheet structures, and so on. Conservative substitution tables are well known in the art (see for example Creighton (1984) Proteins. W.H. Freeman and Company). An overview of physical and chemical properties of amino acids is given in Table C.

TABLE C

Properties of naturally occurring amino acids.

| Charge properties/hydrophobicity | Side Group | Amino Acid |
|---|---|---|
| nonpolar hydrophobic | aliphatic | ala, ile, leu, val |
| | aliphatic, S-containing | met |
| | aromatic | phe, trp |
| | imino | pro |
| polar uncharged | aliphatic | gly |
| | amide | asn, gln |
| | aromatic | try |
| | hydroxyl | ser, thr |
| | sulfhydryl | cys |
| positively charged | basic | arg, his, lys |
| negatively charged | acidic | asp, gly |

Two special forms of homology, orthologous and paralogous, are evolutionary concepts used to describe ancestral relationships of genes.

The term "parologous" relates to gene-duplications within the genome of a species leading to paralogous genes.

The term "orthologous" relates to homologous genes in different organisms due to ancestral relationship. The present invention thus also relates to homologues, paralogues and orthologues of the proteins according to the invention.

"Substitutional variants" of a protein of the invention are those in which at least one residue in said protein amino acid sequence has been removed and a different residue inserted in its place. Amino acid substitutions are typically of single residues, but may be clustered depending upon functional constraints placed upon the polypeptide; insertions will usually be of the order of about 1-10 amino acid residues, and deletions will range from about 1-20 residues. Preferably, amino acid substitutions will comprise conservative amino acid substitutions, such as those described supra.

"Insertional variants" of a protein of the invention are those in which one or more amino acid residues are introduced into a predetermined site in said protein. Insertions can comprise amino-terminal and/or carboxy-terminal fusions as well as intra-sequence insertions of single or multiple amino acids. Generally, insertions within the amino acid sequence will be smaller than amino- or carboxy-terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, $(histidine)_6$-tag, glutathione S-transferase-tag, protein A, maltose-binding protein, dihydrofolate reductase, Tag.100 epitope, c-myc epitope, FLAG®-epitope, lacZ, CMP (calmodulin-binding peptide), HA epitope, protein C epitope and VSV epitope.

"Deletion variants" of a protein of the invention are characterized by the removal of one or more amino acids from said protein. Amino acid variants of a protein of the invention may readily be made using peptide synthetic techniques well known in the art, such as solid phase peptide synthesis and the like, or by recombinant DNA manipulations. The manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

The term "homologues" of an E2F transcription factor are those peptides, oligopeptides, polypeptides, proteins and enzymes which contain amino acid substitutions, deletions and/or additions relative to said E2F transcription factor, providing similar biological activity as the unmodified polypeptide from which they are derived. Preferably said homologues have at least about 90% sequence identity. The invention thus also relates to the use of such homologues of E2F transcription factors in the described methods and more preferably to the use of homologues of the protein represented in SEQ ID NO 2.

"Derivatives" of a protein of the invention are those peptides, oligopeptides, polypeptides, proteins and enzymes which may comprise additional naturally-occurring, altered glycosylated, acylated or non-naturally occurring amino acid residues compared to the amino acid sequence of a naturally-occurring form of said polypeptide. A derivative may also comprise one or more non-amino acid substituents compared to the amino acid sequence of which it is derived, for example a reporter molecule or other ligand, covalently or non-covalently bound to the amino acid sequence such as, for example, a reporter molecule which is bound to facilitate its detection.

An "enzymatically active fragment" of an E2F transcription factor comprise at least five contiguous amino acid residues of said protein but must retain the biological activity of naturally-occurring E2F transcription factor. This term also means any fragment of the protein that is still capable of exerting the function.

The term "cell cycle" means the cyclic biochemical and structural events associated with growth and with division of cells, and in particular with the regulation of the replication of DNA and mitosis. Cell cycle includes phases called: G0, Gap1 (G1), DNA synthesis (S), Gap2 (G2), and mitosis (M). Normally these four phases occur sequentially, however, the cell cycle also includes modified cycles wherein one or more phases are absent resulting in modified cell cycle such as endomitosis, acytokinesis, polyploidy, polyteny, and endoreduplication.

With 'recombinant DNA molecule' or 'chimeric gene' is meant a hybrid DNA produced by joining pieces of DNA from different sources through deliberate human manipulation.

The term "expression" means the production of a protein or nucleotide sequence in the cell. However, said term also includes expression of the protein in a cell-free system. It includes transcription into an RNA product, post-transcriptional modification and/or translation to a protein product or polypeptide from a DNA encoding that product, as well as possible post-translational modifications. Depending on the specific constructs and conditions used, the protein may be recovered from the cells, from the culture medium or from both. For the person skilled in the art it is well known that it is not only possible to express a native protein but also to express the protein as fusion polypeptides or to add signal sequences directing the protein to specific compartments of the host cell, e.g., ensuring secretion of the peptide into the culture medium, etc. Furthermore, such a protein and fragments thereof can be chemically synthesized and/or modified according to standard methods described.

A "vector" as used herein includes reference to a nucleic acid used for transfection or transformation of a host cell and into which a nucleic acid can be inserted. Expression vectors allow transcription and/or translation of a nucleic acid inserted therein. Expression vectors can for instance be cloning vectors, binary vectors or integrating vectors and typically contain control sequences as described supra to ensure expression in prokaryotic and/or eukaryotic cells. Regulatory elements permitting expression in prokaryotic host cells comprise, e.g., the $P_L$, lac, trp or tac promoter in *E. coli*. Examples of regulatory elements permitting expression in eukaryotic host cells are the AOX1 or GAL1 promoter in yeast or the CMV-, SV40-, RSV-promoter, or the CMV-, SV40-enhancer or a globin intron in mammalian and other animal cells. In this context, suitable expression vectors are known in the art such as Okayama-Berg cDNA expression vector pcDV1 (Pharmacia), pCDM8, pRc/CMV, pcDNA1, pcDNA3 (Invitrogen), pSPORT1 (GIBCO BRL). Advantageously, vectors of the invention comprise a selectable and/or scorable marker. Selectable marker genes useful for the selection of transformed plant cells, callus, plant tissue and plants are well known to those skilled in the art. For example, antimetabolite resistance provides the basis of selection for: the dhfr gene, which confers resistance to methotrexate (Reiss, Plant Physiol. (Life Sci. Adv.) 13 (1994), 143-149); the npt gene, which confers resistance to the aminoglycosides neomycin, kanamycin and paromomycin (Herrera-Estrella, EMBO J. 2 (1983), 987-995); and hpt, which confers resistance to hygromycin (Marsh, Gene 32 (1984), 481-485). Additional selectable markers genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and omithine decarboxylase which confers resistance to the ornithine decarboxylase inhibitor, 2-(difluoromethyl)-DL-ornithine or DFMO (McConlogue, 1987, In: Current Communications in Molecular Biology, Cold Spring Harbor Laboratory ed.) or *deaminase* from *Aspergillus terreus* which confers resistance to Blasticidin S (Tamura, Biosci. Biotechnol. Biochem. 59 (1995), 2336-2338). Useful scorable markers are also known to those skilled in the art and are commercially available. Advantageously, said marker is a gene encoding luciferase (Giacomin, PI. Sci. 116 (1996), 59-72; Scikantha, J. Bact. 178 (1996), 121), green fluorescent protein (Gerdes, FEBS Lett. 389 (1996), 44-47) or β-glucuronidase (Jefferson, EMBO J. 6 (1987), 3901-3907).

The vector or nucleic acid molecule according to the invention may either be integrated into the genome of the host cell or it may be maintained in some form extrachromosomally. In this respect, it is also to be understood that the nucleic acid molecule of the invention can be used to restore or create a mutant gene via homologous recombination or via other molecular mechanisms such as for example RNA interference (Paszkowski (ed.), Homologous Recombination and Gene Silencing in Plants. Kluwer Academic Publishers (1994)).

As used herein, a 'host cell' is a cell which contains a vector and supports the expression and/or replication of this vector. Host cells may be prokaryotic cells such as *E. coli* and *A. tumefaciens*, or it may be eukaryotic cells such as yeast, insect, amphibian, plant or mammalian cells. Preferably, host cells are monocotyledonous or dicotyledonous plant cells.

The term "fragment of a sequence" or "part of a sequence" means a truncated sequence of the original sequence referred to. The truncated sequence (nucleic acid or protein sequence) can vary widely in length; the minimum size being a sequence of sufficient size to provide a sequence with at least a comparable function and/or enzymatic activity of the original sequence referred to, while the maximum size is not critical. In some applications, the maximum size usually is not substantially greater than that required to provide the desired activity and/or function(s) of the original sequence. Typically, the truncated amino acid sequence will range from about 5 to about 60 amino acids in length. More typically, however, the sequence will be a maximum of about 50 amino acids in length, preferably a maximum of about 30 amino acids. It is usually desirable to select sequences of at least about 10, 12 or 15 amino acids, up to about 20 or 25 amino acids.

As used herein, the term "plant" includes reference to whole plants, plant organs (such as leaves, roots, stems, etc.), seeds and plant cells and progeny of same. 'Plant cell', as used herein, includes suspension cultures, embryos, meristematic regions, callus tissue, leaves, seeds, roots, shoots, gametophytes, sporophytes, pollen, and microspores. The plants that can be used in the methods of the invention include all plants which belong to the superfamily *Viridiplantae* , in particular monocotyledonous and dicotyledonous plants including a fodder or forage legume, ornamental plant, food crop, tree, or shrub selected from the list comprising *Acacia* spp., *Acer* spp., *Actinidia* spp.,*Aesculus* spp., *Agathis australis, Albizia amara, Alsophila tricolor, Andropogon spp., Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chaenomeles spp., Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Diheteropogon amplectens, Dioclea* spp, *Dolichos* spp., *Dorycnium rectum, Echinochloa pyramidalis, Ehraffia* spp., *Eleusine coracana, Eragrestis* spp., *Erythrina* spp., *Eucalyptus* spp., *Euclea schimperi, Eulalia villosa, Fagopyrum* spp., *Feijoa sellowiana, Fragaria* spp., *Flemingia* spp, *Freycinetia banksii, Geranium thunbergii, Ginkgo biloba, Glycine javanica, Gliricidia* spp, *Gossypium hirsutum, Grevillea* spp., *Guibourtia coleosperma, Hedysarum* spp., *Hemarthia altissima, Heteropogon contortus, Hordeum vulgare, Hyparrhenia rufa, Hypericum erectum, Hyperthelia dissoluta, Indigo incarnata, Iris* spp., *Leptarrhena pyrolifolia, Lespediza* spp., *Lettuca* spp., *Leucaena leucocephala, Loudetia simplex, Lotonus bainesii, Lotus* spp., *Macrotyloma axillare, Malus* spp., *Manihot esculenta, Medicago sativa, Metasequoia glyptostroboides, Musa sapientum, Nicotianum* spp., *Onobrychis* spp., *Omithopus* spp., *Oryza* spp., *Peltophorum africanum, Pennisetum* spp., *Persea gratissima, Petunia* spp., *Phaseolus* spp., *Phoenix canariensis, Phormium cookianum,*

*Photinia* spp., *Picea glauca, Pinus* spp., *Pisum sativum, Podocarpus totara, Pogonarthria fleckii, Pogonarthria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys verticillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp. *Vitis vinifera, Watsonia pyramidata, Zantedeschia aethiopica, Zea mays*, amaranth, artichoke, asparagus, broccoli, brussel sprout, cabbage, canola, carrot, cauliflower, celery, collard greens, flax, kale, lentil, oilseed rape, okra, onion, potato, rice, soybean, straw, sugarbeet, sugar cane, sunflower, tomato, squash, and tea, amongst others. A particularly preferred plant is *Oryza sativa.*

A "plant" as used herein also means a plant cell, a pant tissue or a plant organ. A plant tissue or organ is any plant tissue or any plant organ that can be named as being a part of a plant or part of a plant derived explant.

The term "cotyledon" means the seed leaf that absorbs nutrients. For poaceae and cereals the scutellum is the unique cotyledon that absorbs endosperm.

The term "panicle" as used herein means a flower cluster along the stem of a plant.

Possibly, this flower cluster consists of a number of individual stalks (racemes) each of which has a series of single flowers along its length. For corn, the panicles are also referred to as ears.

The term "tiller" as used herein is a plant shoot: a shoot growing from the base of a stem, especially the stem of a grass.

The term "transformation" as used herein, refers to the transfer of an exogenous polynucleotide into a host cell, irrespective of the method used for the transfer. The polynucleotide may be transiently or stably introduced into the host cell and may be maintained non-integrated, for example, as a plasmid, or alternatively, may be integrated into the host genome. The resulting transformed plant cell can then be used to regenerate a transformed plant in a manner known by a skilled person. *Agrobacterium*-mediated transformation or agrolistic transformation of plants, yeast, moulds or filamentous fungi is based on the transfer of part of the transformation vector sequences, called the T-DNA, to the nucleus and on integration of said T-DNA in the genome of said eukaryote.

With "*Agrobacterium*" is meant a member of the *Agrobacteriaceae*, more preferably *Agrobacterium* or *Rhizobacterium* and most preferably *Agrobacterium tumefaciens.*

With 'T-DNA', or transferred DNA, is meant that part of the transformation vector flanked by T-DNA borders which is, after activation of the *Agrobacterium vir* genes, nicked at the T-DNA borders and is transferred as a single stranded DNA to the nucleus of an eukaryotic cell.

When used herein, with "T-DNA borders", 'T-DNA border region', or "border region" are meant either right T-DNA border (RB) or left T-DNA border (LB). Such a border comprises a core sequence flanked by a border inner region as part of the T-DNA flanking the border and/or a border outer region as part of the vector backbone flanking the border. One element enhancing T-DNA transfer has been characterised and resides in the right border outer region and is called overdrive (Peralta, Hellmiss et al., 1986;van Haaren, Sedee et al., 1987).

With 'T-DNA transformation vector' or 'T-DNA vector' is meant any vector encompassing a T-DNA sequence flanked by a right and left T-DNA border consisting of at least the right and left border core sequences, respectively, and used for transformation of any eukaryotic cell.

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a vector.

As used herein, the term "heterologous" in reference to a nucleic acid is a nucleic acid that is either derived from a cell or organism with a different genomic background, or, if from the same genomic background, is substantially modified from its native form in composition and/or genomic environment through deliberate human manipulation. Accordingly, a heterologous protein although originating from the same species may be substantially modified by human manipulation.

"Transgenic" is used herein to include any cell, cell line, callus, tissue, plant part or plant, the genotype of which has been altered by the presence of the heterologous nucleic acid including those transgenics initially so altered as well as those created by sexual crosses or asexual propagation from the initial transgenic.

(a) High expression of E2Fa in a longitudinal section of the shoot apical meristem (SAM) and surrounding differentiating tissues of radish. Arrowhead points to the SAM.

(b) Homogeneous expression of DPa in the longitudinal section of the SAM and young leaves of radish. Arrowhead points to the SAM.

(c) E2Fa expression in the longitudinal section through a root meristem (RM) of radish.

(d) Homogeneous DPa expression in the longitudinal section through the RM of radish.

(e) Longitudinal section through a hypocotyl of an *Arabidopsis* seedling. E2Fa transcripts are detected in the epidermal and cortical cells. Arrowhead point to the epidermis and cortex tissues.

(f) Longitudinal section through a hypocotyl of an etiolated *Arabidopsis* seedling. Expression is stronger in the hypocotyl hook of dark- than in light-grown seedlings. Arrowhead point to the epidermis and cortex tissues.

Scale bars: 50 μm (a, b), 20 μm (c through f).

Figure 2:
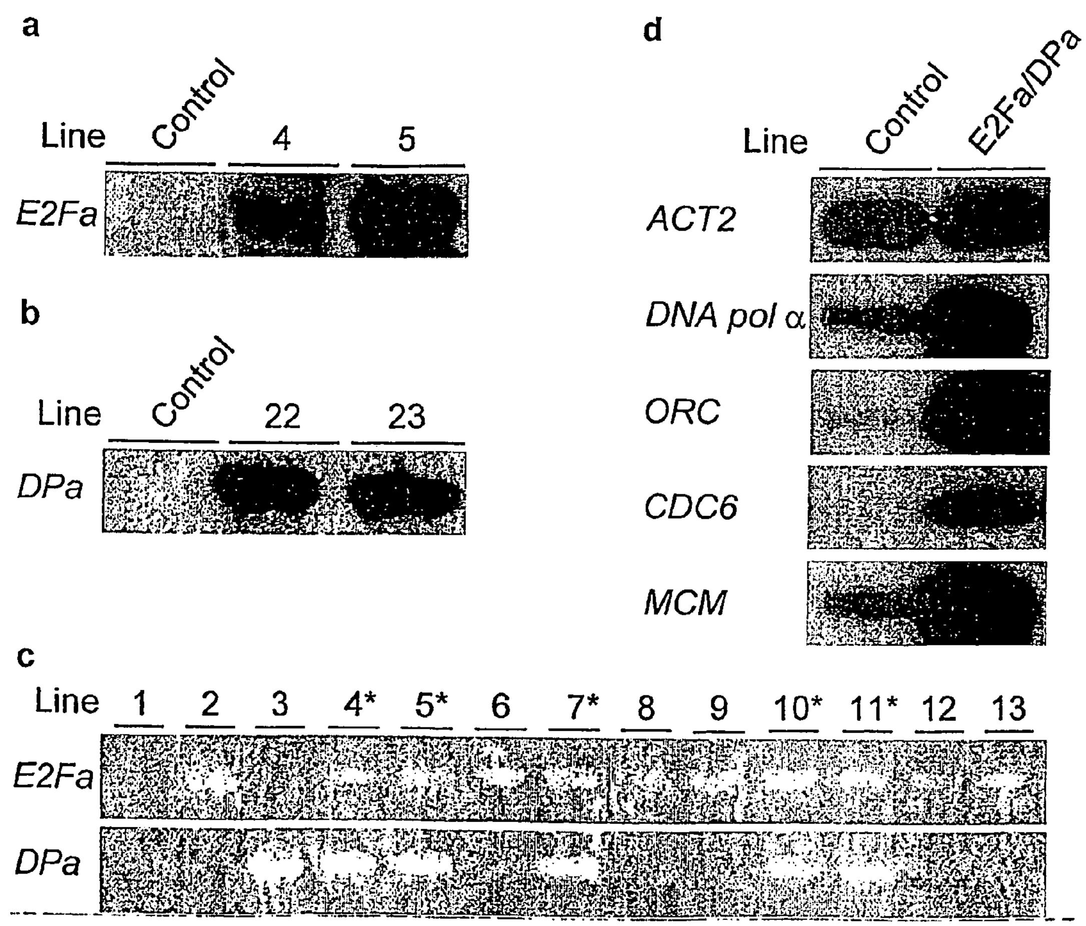

FIG. 2. Molecular analysis of E2Fa- and DPa-overexpressing Arabidopsis plants.

(a) RNA gel blot of independent CaMV 35S E2Fa transgenic plants.

(b) RNA gel blot of independent CaMV 35S DPa transgenic plants.

(c) Linkage of the observed growth arrest with the presence of both CaMV 35S E2Fa and CaMV 35S DPa transgenes. 1, Wild-type plant; 2, cross between a CaMV 35S E2Fa plant and a control plant; 3, cross between a CaMV 35S DPa plant and a control plant; 4 to 13, individual siblings of a cross between a homozygous CaMV 35S E2Fa plant and a heterozygous CaMV 35S DPa. Lines marked with * showed curled leaves and cotyledons and were arrested at the seedling stage. Presence of transgenes was tested by PCR.

(d) Transcript levels of S-phase genes in control and 35S CaMV E2Fa/DPa plants.

Figure 3:
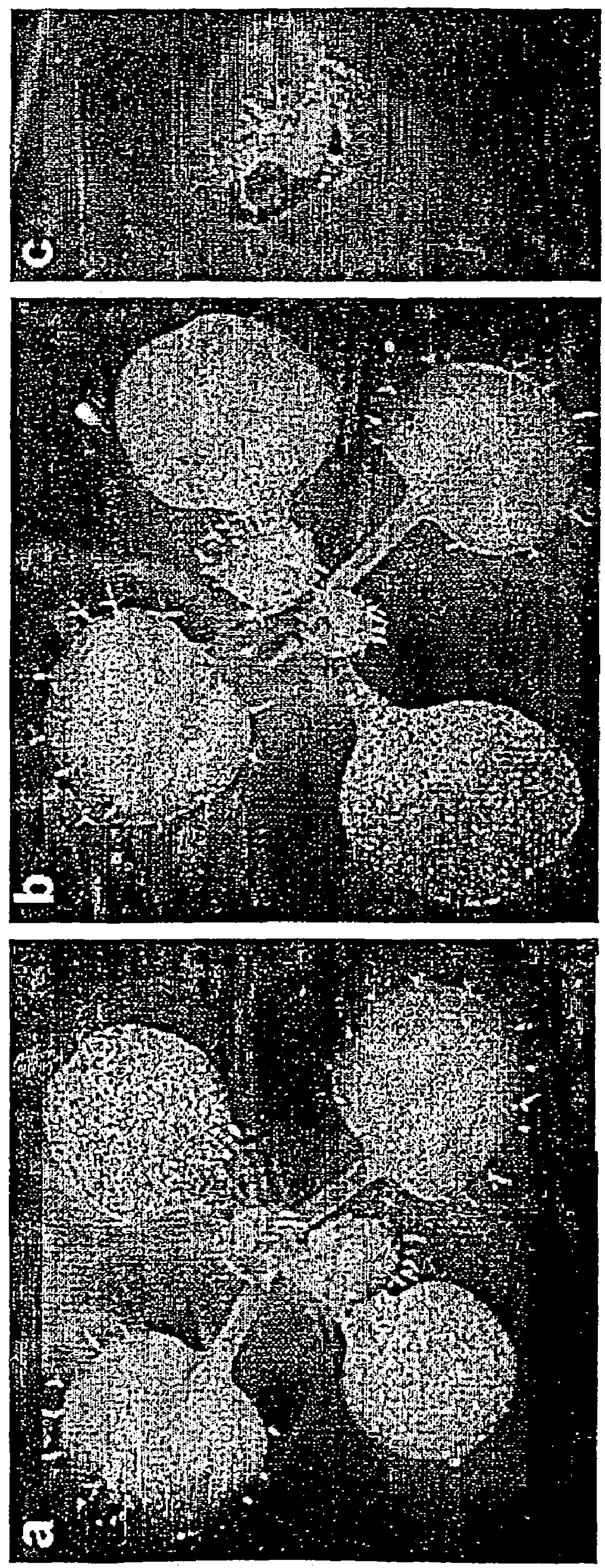

FIG. 3. Phenotype of E2Fa- and DPa-overexpressing plants.

(a) Untransformed control.

(b) E2Fa-overexpressing plant.

(c) E2Fa/DPa-overexpressing plant. All plants were photographed at the same magnification 12 days after sowing.

Scale bar: 0.25 cm. The two cotyledons in (a) and (b) are shown in the upper right and lower left corner.

Figure 4:
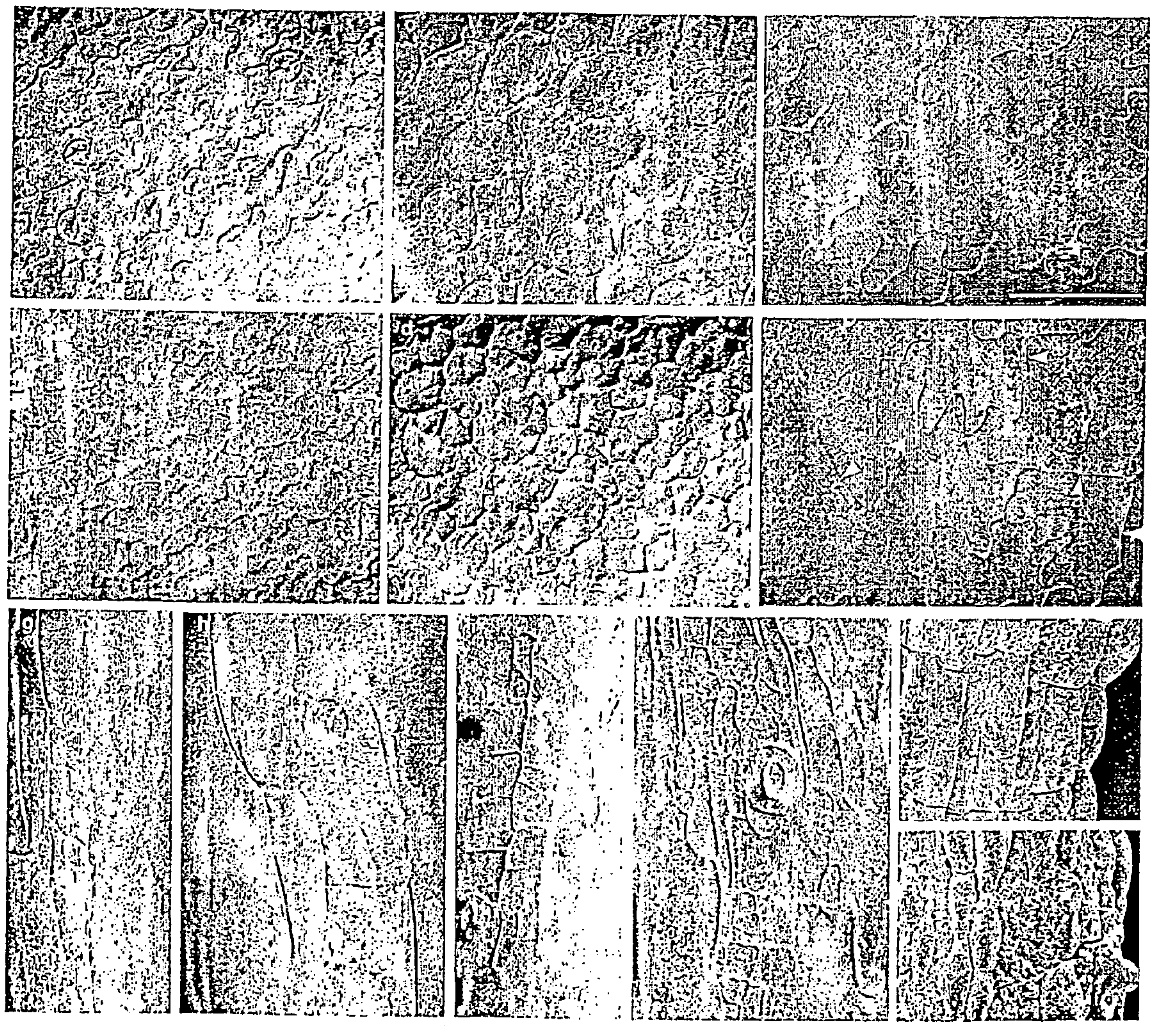

FIG. 4. Microscopic analysis of E2Fa- and E2Fa/DPa-overexpressing plants.

(a), (e) Abaxial epidermis of a 5-day-old and 3-week-old control plants, respectively.

(b), (f), Abaxial epidermis of a 5-day-old and 3-week-old E2Fa plant, respectively.

(c), (d) Palisade of a 5-day-old control and E2Fa plants, respectively.

(g) Hypocotyl of 12-day-old control plant.

(h) Hypocotyl of 12-day-old E2Fa plant.

(i) Hypocotyl of 12-day-old E2Fa/DPa plant;

(j) Hypocotyl of a 3-week-old E2Fa/DPa plant;

(k), (i) Scanning micrographs of (g) and (i).

Arrowheads in (d) and (f) point to novel synthesized cell walls; asterisks in (g) and (h) indicate cell files in which stomata are formed.

Scale bars: 100 μm (a through d, k, l) and 50 μm (e through j).

Figure 5:
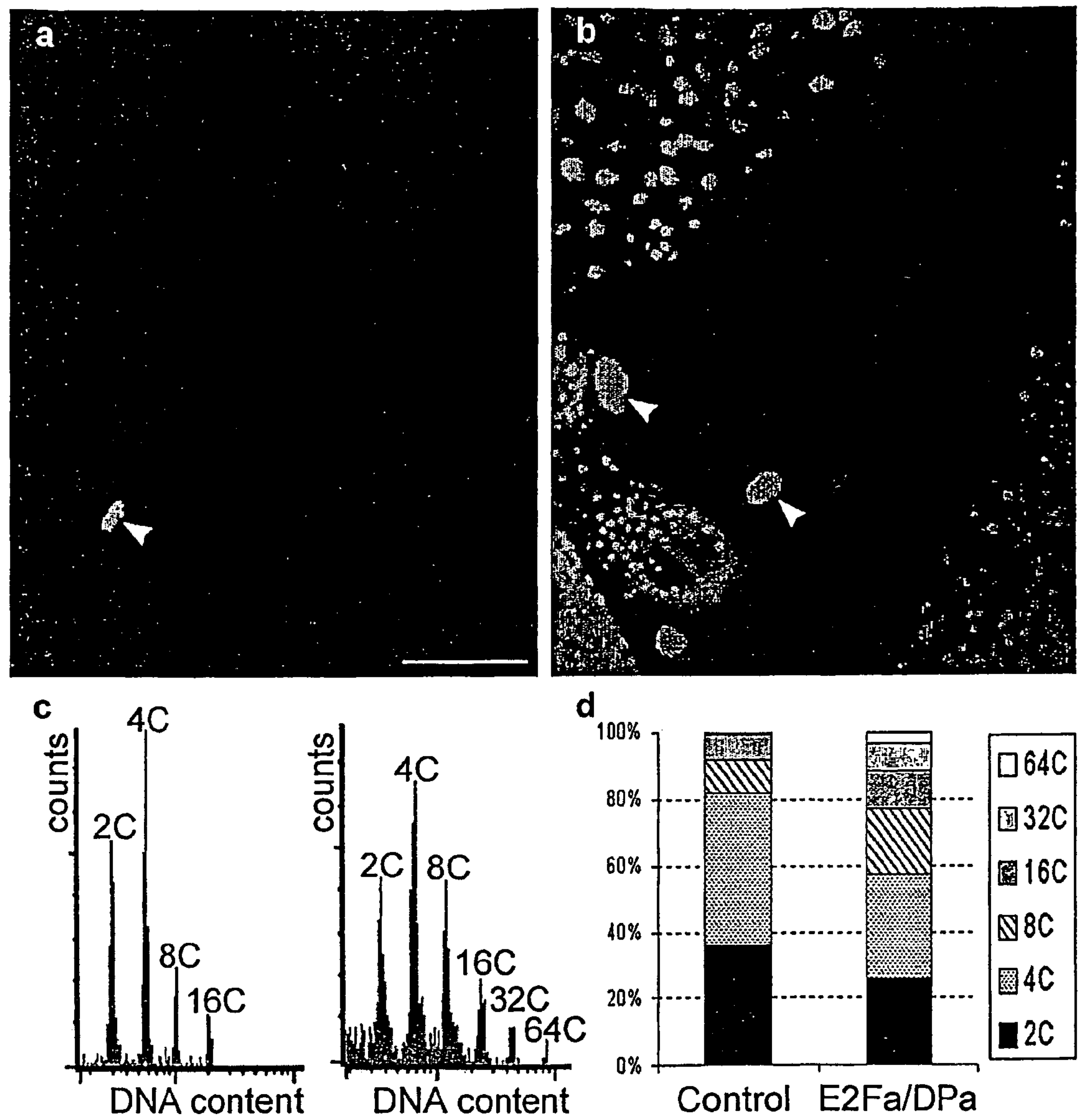

FIG. 5. DNA ploidy level in control and CaMV 35S E2Fa/DPa transgenic plants.

(a) Trichome of a control plant.

(b) Trichome of a E2Fa/DPa transgenic plant. Arrowheads point to the nucleus.

(c) Ploidy distribution of control (left) and E2Fa/DPa transgenic seedlings (right) harvested 12 days after germination.

(d) Quantification of the results shown in (c).

Scale bar: 50 μm; (a) and (b) have same magnification.

FIG. 6. The nucleotide sequence of the Arabidopsis E2Fa gene (SEQ ID NO 1) and the amino acid sequence (SEQ ID NO 2) of the open reading frame encoding the Arabidopsis E2Fa protein.

FIG. 7. The nucleotide sequence of the Arabidopsis DPa gene (SEQ ID NO 3) and the amino acid sequence (SEQ ID NO 4) of the open reading frame encoding the Arabidopsis DPa protein.

FIG. 8. The nucleotide sequence of a splice variant of the Arabidopsis E2Fa gene (SEQ ID NO 19) and the amino acid sequence (SEQ ID NO 20) of the open reading frame encoding the Arabidopsis E2Fa variant protein.

FIG. 9. Sequence alignment of the two E2Fa proteins of the present invention, SEQ ID NO 2, compared with SEQ ID NO 20 (CDS009 E2Fa) and compared with the sequence form the public database under the Genbank accession number CAC15486. Sequence alignment was done with the program Align X as a component of the Vector NTI Suite 5.5 software, using the Clustal W algorithm (NucleicAcid Research, 22 (22): 46734680, 1994).

FIG. 10. Sequence alignment of the two E2Fa nucleic acids of the present invention, SEQ ID NO 1, compared with SEQ ID NO 19 (CDS009 E2Fa) and with the sequence form the public database under the Genbank accession number AJ294534. Sequence alignment was done with the program Align X as a component of the Vector NTI Suite 5.5, using the Clustal W algorithm (NucleicAcid Research, 22 (22): 4673-4680,1994).

Figure 11:
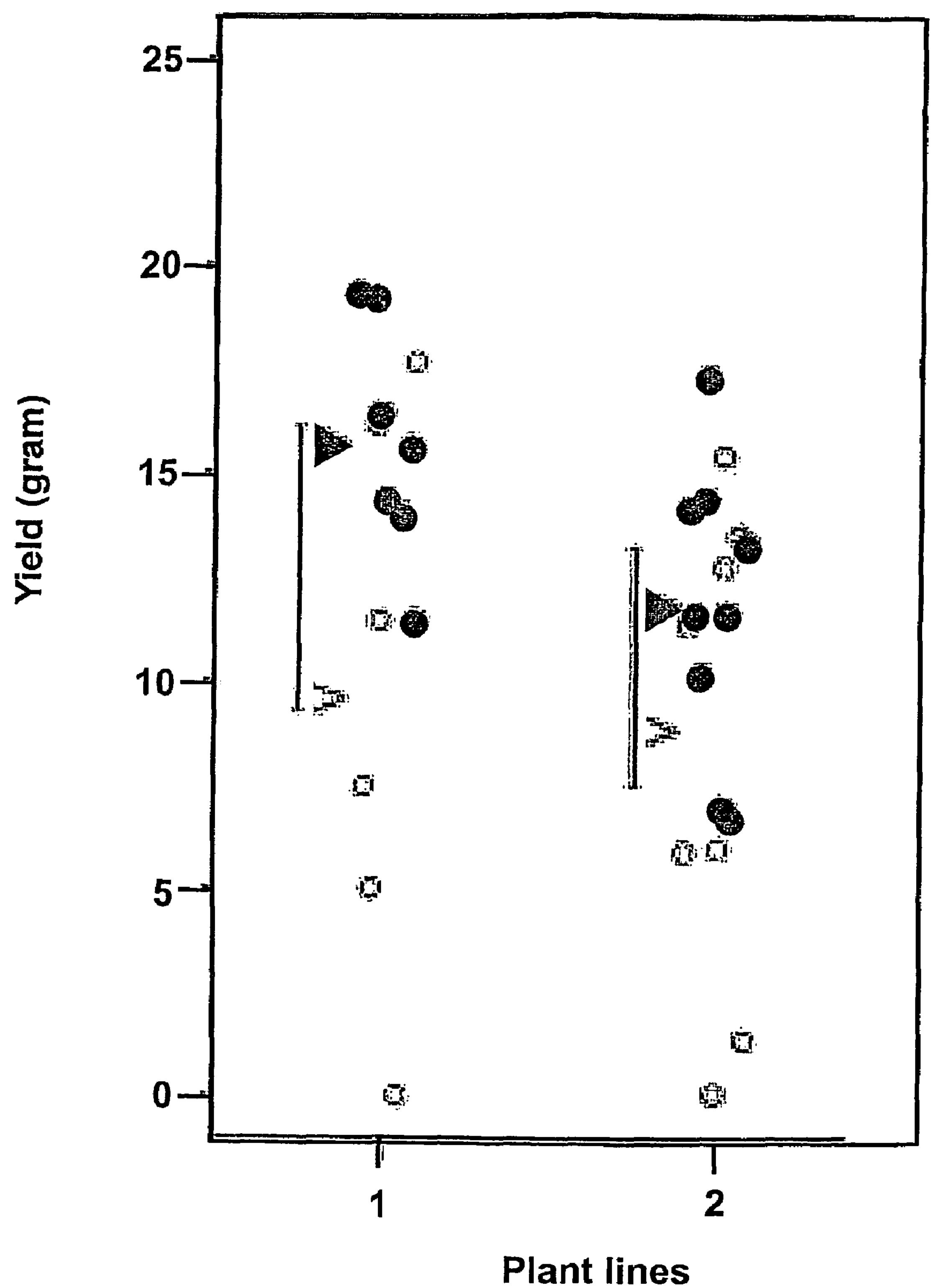

FIG. 11. Presentation of the seed yield evaluation data of two transgenic rice lines, transformed with the E2Fa gene as encoded by SEQ ID NO 19. The two plant lines are nominated as 1 and 2 on the X-axis. For each of the two rice lines, the seeds of several positive plants (filled circles) and several negative plants (open circles) were harvested and weighted. Seed yield is measured in grams and the corresponding values are represented on the Y-axis. The "least significant difference" is shown as a vertical bar and the average values of the positive plants and the negative plants is shown as a filled or open arrowhead respectively.

EXAMPLES

Example 1

Overexpression of E2Fa and DPa in Arabidopsis

Regeneration of Transgenic Plants and and Molecular Analysis

The E2Fa- and DPa-coding regions were amplified by PCR with the

```
                                    (SEQ ID NO 5)
5'-GGCCATGGCCGGTGTCGTACGATCTTCTCCCGA-3'
and
                                    (SEQ ID NO 6)
5'-GGGGATCCTCATCTCGGGGTTGAGT-3'
or
                                    (SEQ ID NO 7)
5'-GGCCATGGAGTTGTTTGTCACTCC-3'
and
                                    (SEQ ID NO 8)
5'-GGAGATCTTCAGCGAGTATCAATGG-3'
```

primers, respectively. The obtained E2Fa PCR fragment was cut with NcoI and BamHI and the DPa fragment was digested with NcoI and BgIII. Subsequently, the restriction fragments were cloned between the CaMV 35S promoter and the nopaline synthase (NOS) 3' untranslated region in the NcoI and BamHI sites of PH35S (Hemerly et al., 1995), resulting in the PH35SE2Fa and PH35SDPa vectors. The CaMV 35S-E2Fa-Nos cassette was released by EcoRI and XbaI and cloned into the EcoRI and XbaI sites of pBinPLUS (van Engelen et al., 1995), resulting in the pBINE2Fa vector, whereas the CaMV 35S-Dpa-Nos cassette was released by EcoRi and XbaI and made blunt-ended into the SmaI site of PGSC1704, resulting in the PGSCDPa vector. Both pBinE2Fa and PGSCDPa were mobilized by the helper plasmid pRK2013 into the *Agrobacterium tumefaciens* C58C1Rif$^R$ harbouring the plasmid pMP90 (Koncz and Schell, 1986). *Arabidopsis thaliana* (L.) Heynh. ecotype Columbia were transformed by the floral dip method (Clough and Bent, 1998). Transgenic CaMV 35S E2Fa and CaMV 35S DPa plants were obtained on kanamycin- or hygromycin-containing medium, respectively. For all analysis, plants were grown under 16-hr light/8-hr dark photoperiod at 22° C. on germination medium (Valvekens et al., 1988). Northern blot analysis was performed as described (De Veylder et al., 2001). Linkage of the phenotype with the presence of transgenes was tested by grinding individual plants in 400 μl DNA extraction buffer (200 mM Tris-HCl, pH 7.5, 205 mM NaCl, 25 mM ethylenediaminetetraacetic acid, 0.5% sodium dodecyl sulfate). Extracts were centrifuged at 18,000×g for 2 minutes. DNA was precipitated by adding 300 μl isopropanol to 300 μl extract and centrifugation for 10 minutes at 18,000×g. The pellet was rinsed with 70% ethanol, air dried, and resuspended in 100 μl water. For PCR analysis, 5 μl was used with above-mentioned primers. Because the transgenes do not contain introns, they could be distinguished from the endogenous E2Fa and DPa gene based on their size.

Selection of Trans-Genic Lines

To evaluate the importance of E2Fa and DPa expression in dividing and endoreduplicating cells, transgenic *Arabidopsis thaliana* plants were generated that contained either the E2Fa or the DPa gene under the control of the constitutive cauliflower mosaic virus (CaMV) 35S promoter. Out of multiple transgenic lines, two independent CaMV 35S E2Fa (FIG. 2*a*) and two CaMV 35S DPa (FIG. 2*b*) lines were selected, containing only one T-DNA locus. Whereas the DPa transgenic plants were morphologically identical to untransformed control plants, 3-week-old E2Fa plants had enlarged cotyledons (FIGS. 3*a* and 3*b* and Table D).

TABLE D

Adaxial epidermal cell size and cell number in cotyledons of E2Fa-overexpressing plants. These data show that transgenic plants have more ectopic cell division compared to the wild type plants.

| Line | | |
|---|---|---|
| | Cotyledon[a] 3 weeks after sowing Size (mm2) | |
| Wild type | 5.3 ± 0.3 | |
| E2Fa line 4 | 7.2 ± 0.3 | |
| E2Fa line 5 | 7.2 ± 0.3 | |
| | Adaxial epidermal cells 3 weeks after sowing | |
| | Size (μm2) | Estimated number |
| Wild type | 4612 ± 268 | 1204 ± 104 |
| E2Fa line 4 | 2712 ± 272 | 2904 ± 236 |
| E2Fa line 5 | 2190 ± 183 | 3389 ± 366 |
| | Cotyledon prior to germination | |
| | Size (mm2) | Number[b] |
| Wild type | 0.099 ± 0.002 | 612 ± 12 |
| E2Fa line 4 | 0.089 ± 0.005 | 610 ± 35 |
| E2Fa line 5 | 0.068 ± 0.003 | 525 ± 32 |

The indicated values are mean ± SE.

[a]Untransformed and transgenic plants (n = 12) were grown in the same Petri dish to exclude differences in growth conditions. The observed increase in cotyledon size was confirmed in at least three independent experiments. The number of adaxial epidermal cells was determined by the ratio of cotyledon size to adaxial epidermal cell size, which was measured for at least 50 cells in each cotyledon.

[b]The number of adaxial cells prior to germination was measured by counting all cells of at least five different cotyledons per line.

The indicated values are mean ±SE. [a]Untransformed and transgenic plants (n=12) were grown in the same Petri dish to exclude differences in growth conditions. The observed increase in cotyledon size was confirmed in at least three independent experiments. The number of adaxial epidermal cells was determined by the ratio of cotyledon size to adaxial epidermal cell size, which was measured for at least 50 cells in each cotyledon. [b]The number of adaxial cells prior to germination was measured by counting all cells of at least five different cotyledons per line.

Example 2

Scanning Electron Microscopy

Method

For scanning electron microscopy, seedlings were fixed overnight in 4% paraformaldehyde and 1% glutaraldehyde in 0.1 M phosphate buffer (pH 7.2), followed by a post-fixation step in 2% osmiumtetroxide and by a graded ethanol series. Critical-point drying was carried out in liquid carbon dioxide. These seedlings were mounted on stubs, sputter-coated with gold, and examined with a scanning microscope (JEOL Ltd., Tokyo, Japan) with an accelerating voltage of 10 kV. Fluorescent staining of nuclei was performed by fixing the seedlings in a mixture of 9:1 (v/v) ethanol and acetic acid. After the samples had been rinsed, they were stained for 24 hours with 0.1 μg/ml 4',6-diamidino-2-phenylindole and analyzed with an inverted confocal microscope LSM510 (Zeiss, Jena, Germany) with a X20 plan-apochromat objective.

Cell Morphology in Cotyledons of 35S-E2Fa Plants

Larger cotyledons can result from larger cells or from a higher number of cells. To discriminate between these possibilities, adaxial epidermal cell size was measured. Remarkably, in the strongest E2Fa-overexpressing line cotyledon cells were less than half the size of control cells. As a consequence of an increase in cotyledon size and a reduction in cell size, transgenic cotyledons contained almost 3-fold as many cells as control plants (Table D). Because the number of epidermal cells in cotyledons was approximately the same in seeds from control and transgenic plants (Table D), extra cells must originate from additional cell divisions that occur after seed germination. Five days after sowing, the adaxial epidermal cotyledon cells of wild-type plants were differentiated into puzzle-shaped pavement cells and stomata (FIG. 4*a*). In 5-day-old E2Fa-overexpressing lines only polygonal cells and few stomata could be observed (FIG. 4*b*). Similarly, instead of typical palisade tissue consisting of round cells with intercellular spaces, CaMV 35S E2Fa palisade cells were still polygonal without intercellular spaces and dividing (FIGS. 4*c* and 4*d*). These results indicate that enhanced E2Fa levels prolong the period of cell division, a situation reminiscent to that in mammals where overexpression of E2F1 inhibits differentiation of cells into myoblasts and megakaryocytes (Wang et al., 1995; Guy et al., 1996).

Cell Morphology in the Hypocotyl of 35S-E2Fa Plants

In the hypocotyl of 35S-E2Fa transgenic plants, cell files consisting of normal epidermal cells alternate with cell files clearly showing extra cell divisions, suggesting that E2Fa works in a cell type-specific manner (FIGS. 4*g* and 4*h*). Cell files that divide ectopically are those in which normally stomata are formed (Berger et al., 1998), indicating that E2F and/or E2Fa/DPa can sustain only cell division in cells that are competent to divide.

Analysis of E2Fa Overexpression Effect in Differentiated Cells

In 3-week-old control plants, all epidermal cotyledon cells are fully differentiated and are puzzle shaped (FIG. 4*e*). In contrast, in E2Fa-overexpressing cotyledons of the same age numerous newly formed cell walls with a straight appearance are observed (FIG. 4*f*). Thus, E2Fa can stimulate differentiated cells to re-enter the cell cycle program.

Cell Morphology Comparison in E2Fa and E2Fa/DPa Overexpressing Lines

Microscopic analysis showed that the phenotype seen in the E2Fa-overexpressing lines was strongly enhanced in the CaMV 35S E2Fa/DPa plants. Cotyledons and leaves of 2-week-old plants consisted completely of small irregularly shaped cells, which had never been seen in wild-type tissues of the same age (data not shown). Also in the hypocotyl, many more cell divisions were observed, resulting in islands of small irregular cells (FIG. 4*i*). This phenotype became more pronounced in older hypocotyls (FIG. 4*j*). Scanning electron microscopy showed that the typical epidermal differentiation pattern found in wild-type hypocotyls was totally disrupted, displaying a mixture of small isodiametric cells and elongated bulging cells (FIGS. 4*k* and 4*l*). Therefore the E2F and DP overexpression can be used to alter the cell shape.

Example 3

In situ Hybridization

Method

In situ hybridizations were performed as described (de Almeida Engler et al., 1991). Not only Arabidopsis thaliana but also Raphanus sativus (radish) seedlings were used to obtain more tissue for more precise transcript localization. Full-length E2Fa- and DPa-coding sequences were used to generate [$^{35}$S]-labeled RNA probes. No signal was observed in control hybridizations. Micrographs were obtained by overlaying bright- and dark-field digital images.

Tissues for histological examination were placed overnight in ethanol to remove chlorophyll, subsequently cleared, mounted on a microscope slide, and stored in lactic acid for microscopy. Cells were observed with differential interference contrast optics on a DMLB microscope (Leica, Wetzlar, Germany).

Localisation of E2Fa and DPa Transcripts

Figure 1:
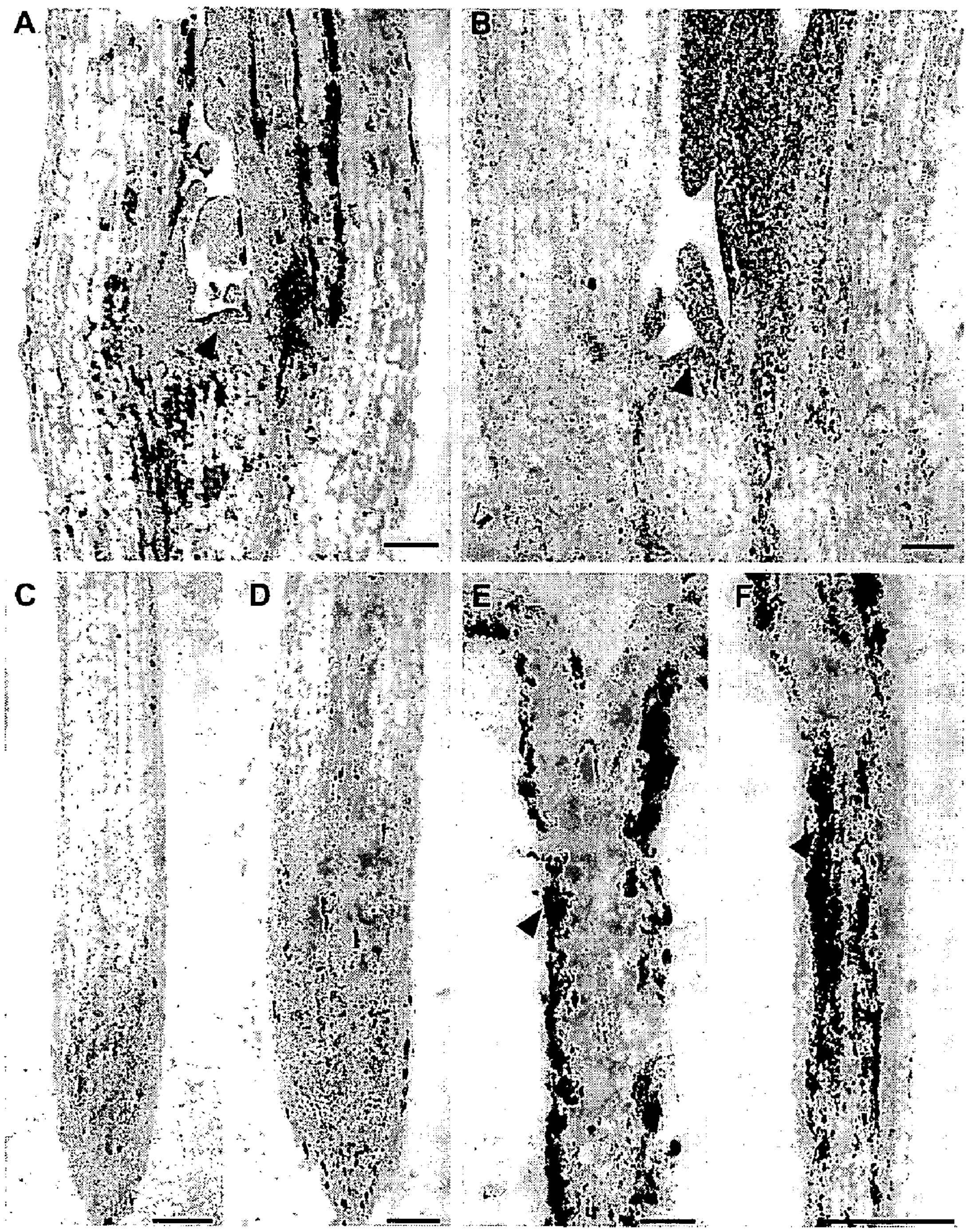
FIG. 1. In situ localization of E2Fa and DPa mRNA. Hybridization signals are seen as black dots.

In this way, the presence of both E2Fa and DPa transcripts was revealed in the shoot apical meristem and surrounding differentiating tissues (FIGS. 1*a* and 1*b*). In the root, the hybridization signals were the strongest in the root apical region where cells divide actively and became weaker as cells exited the meristematic region (FIGS. 1*c*, and 1*d*). The co-expression of E2Fa and DPa in dividing tissues suggests that the E2Fa/DPa complex is required for cell cycle progression. E2Fa transcripts were detected also in the epidermis and cortex of the hypocotyl of 5-day-old light-grown plants (FIG. 1*e*). At this stage, the cortex is devoid of cell division, but undergoes extensive endoreduplication, which is enhanced in dark-grown plants (Gendreau et al., 1997; Raz and Koorneef, 2001). Likewise, the E2Fa hybridization signal was stronger in the cortical hypocotyl cells of dark-grown plants (FIG. 1*f*), indicating that E2Fa could play a role in regulating endoreduplication.

Example 4

Flow Cytometric Analysis

Method

Plants were chopped with a razor blade in 500 μl of 45 mM $MgCl_2$, 30 mM sodium citrate, 20 mM 3-(N-morpholino) propanesulfonic acid (pH 7), and 1% Triton X-100 (Galbraith et al., 1991). The supernatant was filtered over a 30-μm mesh and 1 μl of 4',6-diamidino-2-phenylindole from a stock of 1 mg/ml was added. The nuclei were analyzed with the BRYTE HS flow cytometer and the WinBryte software (Bio-Rad, Hercules, Calif., USA).

Analysis of Nuclei

Wild-type Arabidopsis pavement cells display a broad variation in nuclear size because of the occurrence of endoreduplication (Melargno et al., 1993). In E2Pa/DPa transgenic plants, a majority of small nuclei are observed in cotyledon pavement cells, suggesting that in this tissue endoreduplication is suppressed (data not shown). In contrast, cortical and palisade cells of the hypocotyl and cotyledon, respectively, were enriched with large nuclei. The nuclear size of mature trichomes had increased dramatically (FIGS. 5*a* and 5*b*) as well. These data indicate that besides triggering cell division, E2Fa/DPa induces endoreduplication in a cell-type-specific way.

Flow-Cytometric Analysis

Extensive endoreduplication in the CaMV 35S E2Pa/DPa plants was confirmed by flow cytometric analysis. Two-week-old transgenic seedlings showed two additional endocycles when compared to control plants (FIGS. 5*c* and 5*d*). Also in *Drosophila* ectopic expression of E2F/DP was sufficient to trigger precocious DNA replication in endoreduplicating tissues (Britton and Edgar, 1998). This replication may be mediated via the transcriptional induction of Cyclin E, leading to the formation of the S phase-specific cyclin E/CDK2 complex which is a central regulator for endoreduplication (Edgar and Orr-Weaver, 2001) Although no clear homologue of cyclin E had been identified in the *Arabidopsis* genome, the activation of an S phase-specific CDK complex in the maize endosperm upon the onset of endoreduplication (Grafi and Larkins, 1995) suggests that plants regulate their endocycle in a way similar to that of Drosophila. Also, inactivation of the maize Rb homologue by phosphorylation supports that E2Fa/DPa expression plays a role in the plant endocycle (Grafi et at., 1996).

Ploidy Levels

Although the effects of E2Fa/DPa overexpression in epidermal and ground tissue cells seem to be different, the observed phenotypes arise probably through a common mechanism. The increase in ploidy level in the ground tissue indicates that ectopic E2Fa/DPa stimulates cell cycle proliferation by triggering S phase entry. Whereas after DNA duplication the epidermal cells can proceed into mitosis, ground tissue cells may lack an important factor for progression through M phase and may be stimulated to re-enter the S phase, leading to increases in ploidy levels. Alternatively, the mitotically dividing cells might contain an endoreduplication inhibitor. S phase entry mediated by E2Fa/DPa may be due to the inactivation of Rb by out-titration, thereby relieving the Rb-mediated transcriptional repression of S phase-specific genes.

Example 5

Reverse Transcriptase-Mediated PCR Analysis

Method

RNA was isolated from plants 8 days after sowing using the Trizol reagent (Amersham Pharmacia Biotech, Little Chalfont, UK). First-strand cDNA was prepared from 3 μg of total RNA with the Superscript RT II kit (Gibco BRL, Gaithersburg, Md., USA) and oligo(dT) (Chabouté et al., 2000) according to the manufacturer's instructions. A 0.25-μl aliquot of the total reverse transcription reaction volume (20 pl) was used as a template in a semi-quantitative RT-mediated PCR amplification, ensuring that the amount of amplified product remained in linear proportion to the initial template present in the reaction. Ten microliters from the PCR reaction was separated on a 0.8% agarose gel and transferred onto Hybond $N^+$ membranes (Amersham Pharmacia Biotech). The membranes were hybridized at 65° C. with fluorescein-labeled probes (Gene Images random prime module; Amersham Pharmacia Biotech). The hybridized bands were detected with the CDP Star detection module (Amersham Pharmacia Biotech). Primers used were 5'-TATGGCTGTCTGGGGTTTC-3' (SEQ ID NO 9) and 5'-CAACTTGAACGTGTGGTTGG-3' (SEQ ID NO 10) for DNA pol a (GenBank accession no. AB020742), 5'-TCGAGTCGGT-TGGAAGAAAG-3' (SEQ ID NO 11) and 5'-CTCAT GAAC-CATAGCCGTCA-3' (SEQ ID NO 12) for ORC (AL049730), 5'-GCACCGTCAA CTGTTGTTTG-3' (SEQ ID NO 13) and 5'-CMGCCTCTCCTGCAGAATC-3' (SEQ ID NO 14) for CDC6 (AC005496), 5'-AGGCTAATGAGGGAGGGGTA-3' (SEQ ID NO 15) and 5'-GGMCTGGCCTCATTTGTGT-3' (SEQ ID NO 16) for MCM5 (AC004483), and GTGC-CAATCTACGAGGGTTTC (SEQ ID NO 17) and CMTGG-GACTMAACGAAAA (SEQ ID NO 18) for ACT2 (U41998).

Transcript Level Comparison in Control and E2FaIDPa Plants

Previously, the E2F consensus-binding sequence has been shown to be conserved in plants and mammals (Chaboute et al., 2000). These sequences can be found in the promoters of Arabidopsis genes of which the mammalian counterparts are regulated by E2F/DP (Leone et al., 1998) and include DNA pol α, ORC, MCM, and CDC6. The transcript level of these genes was compared in control and E2Fa/DPa transgenic plants by semi-quantitative reverse-transcription (RT)-PCR analysis. Whereas the expression level of the control gene (actin 2) was not influenced by E2Fa/DPa overexpression, all S phase genes were dramatically up-regulated (FIG. 2*d*). These data demonstrate that E2Fa/DPa regulates the expression of S phase genes in Arabidopsis and suggests that the observed phenotypes result from mis-expression of these genes.

Example 6

Crossing Experiments of Overexpressing E2Fa and DPa Lines

To analyze whether in plants E2F and DP proteins co-operate, plants homozygous for the CaMV 35S E2Fa gene were crossed with heterozygous CaMV 35S DPa lines. Half of the offspring developed normally, whereas 50% of the plants displayed cotyledons and leaves curled along their proximal-distal axis (FIG. 3*c*). Polymerase chain reaction (PCR) analysis on individual plants confirmed that the plants with the curled leaf phenotype contained both the CaMV 35S-E2Fa and CaMV 35S-DPa constructs, whereas the phenotypically normal siblings contained the CaMV 35S E2Fa gene only (FIG. 2*c*).

Example 7

Ectopic Expression of E2Fa/DPa and Effect on Plant Growth

Ectopic expression of E2Fa/DPa results in uncontrolled cell proliferation in differentiated tissues. Consequently, plants arrest in growth early during post-embryonic development. Therefore, the E2Fa/DPa transcription factor is a crucial component that regulates cell division in plants. Its activity has to be controlled in a stringent way. The above-mentioned growth inhibitory effect is in sharp contrast to the phenotype found upon overexpression of the cyclins Arath; CYCB1;1 and Arath;CYCD;2, both promoting plant growth (Doerner et al., 1996; Cockcroft et al., 2000). A major difference between the cyclin-overproducing lines and the E2Fa/DPa transgenic plants is that the former do not proliferate in otherwise differentiated tissues. Thus, in contrast to CYCD2;1 and CYCB1;1, E2Fa/DPa overrides the signals that regulate cell differentiation. The observed negative effect on growth shows that the correct balance between division and differentiation is vital for plant development. Plants may arrest in growth as a consequence of their delayed differentiation or because the required essential cell-signaling between different tissue layers is disturbed. We postulate that plants regulate their differentiation through the modulation of E2Fa/DPa activity. The decision between proliferation and differentiation relies upon the concerted expression of genes determining cell fate. The miss-expression of cell cycle genes induced by E2Fa/DPa could repress the induction of genes needed for differentiation, implying that cell differentiation requires inactivation of E2Fa/DPa transcriptional activity. The accumulation of active Rb proteins in differentiating leaf tissues suggests that, as in mammals, this inactivation is controlled by Rb (Huntley et al., 1998). Nevertheless, our data indicate that the E2Fa/DPa pathways may be used to direct cell division in plants in a specific manner, allowing yield and architecture to be adjusted.

Example 8

Ectopic Expression of E2Fa in Rice Plants

In dicotyledonous plants, overexpression of E2Fa gene leads to enlarged cotyledons. Contrarily to dicotyledonous plants, where the meristem enlarges between 2 cotyledons, in monocotyledonous the enlarging meristem appears laterally oriented to the scutellum. As the scutellum differentiates, the coleoptile is formed and surrounds the shoot apical meristem (SAM), taking a tubular shape. The SAM initiates leaves, each opposite to the previous one. This vegetative meristem is first transformed into an inflorescence meristem, which than generates the floral meristem. To analyze the effect of overexpression of E2Fa in monocotyledonous plants, the gene was cloned and operably linked to the oleosin promoter, in order to obtain a construct expressible in monocot seeds.

Cloning of E2Fa in the Rice Expression Vector

The inventors isolated a splice variant of the E2F as represented in SEQ ID NO 1. This splice variant is represented herein as SEQ ID NO 19 and differs only in two codons from SEQ ID NO 1, resulting in the alternative, smaller E2Fa protein as represented herein as SEQ ID NO 20. The isolated E2Fa splice variant (SEQ ID NO 19) was given the internal designation number CDS009 and was cloned in the vector p0426 carrying a selectable marker and the oleosin promoter for seed specifc expression of the transgene E2Fa. The resulting plant expression vector was given the internal reference number p1134.

DNA Manipulation

All DNA procedures were performed according to standard protocols (Maniatis T, Fritsch EF and Sambrook J (1982) Molecular Cloning: a laboratory manual, Cold Spring Harbor Laboratory Press, CSH, New York).

Cloning of E2F/CDS009

The *Arabidopsis* E2F sequence (Accession Number: AJ294534) was amplified from a *Arabidopsis* Thaliana cDNA library cell suspension cultures by PCR using Platinum Pfx DNA polymerase (Invitrogen) and the following primers: Sense, including attB1 5'GGGGACAAGTTTGTA-CAAAAAAGCAGGCTTCACMTGTAT-TGCTCTTCTTCGATG C 3' (SEQ ID NO 21) and Anti-sense, including attB2 5'GGGGACCACTTTGTACAAG AAAGCTGGGTGCTTGGTGTCATCTTGAGAATAG3' (SEQ ID NO 22) Conditions for PCR were as follows: 1 cycle of 2 minutes denaturation at 94° C., 35 cycles of 1 minute denaturation at 94° C., 1 minute annealing at 58° C. and 2 minutes amplification at 68° C., and 1 cycle of 5 minutes at 68° C. A prominent fragment of about the expected size was isolated from gel and purified using the Zymoclean Gel DNA Recovery Kit (Zymo Research, Orange, Calif.).

The purified PCR fragment was used in a standard Gateway™0 BP reaction (Invitrogen) using pDONR201 as a recipient vector. The identity and basepair composition of the insert was confirmed by sequencing. The resulting plasmid was quality tested using restriction digests and was given the designation p0426 (entry clone). pDONR201, a vector making up part of the Gateway™ cloning technology, was obtained from Invitrogen.

P0426, according to the Gateway™ terminology, is an "entry clone", and was used as such in a standard Gateway™ LR reaction, with a destination vector carrying the pOleosin. The vector resulting from the Gateway™ LR reaction was p1134. This vector was controlled by restriction digest analysis and was used in the transformation of Arabidopsis thaliana. This vector contained as functional elements within the T-DNA region a selectable marker gene and a "Gateway cassette" intended for LR cloning of sequences of interest. Expression of these sequences of interest, upon being recombined into p1134, was driven by the oleosin promoter Rice Transformation Mature dry seeds of the rice japonica cultivar Taipei were dehusked. Sterilization was carried out by incubating for one minute in 70% ethanol, followed by 30 minutes in 0.2%HgCl2, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks the calli were multiplied or propagated by subculture on the same medium for another 2 weeks. Embryogenic callus pieces were sub-cultured on fresh medium 3 days before co-cultivation (to boost cell division activity). *Agrobacterium* strain LBA4404 harboring binary T-DNA vectors were used for cocultivation. *Agrobacterium* was inoculated on AB medium with the appropriate antibiotics and cultured for 3 days at 28° C. The bacteria were then collected and suspended in liquid co-cultivation medium to a density (OD600) of about 1. The suspension was then transferred to a petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a suitable concentration of the selective agent. During this period, rapidly growing resistant callus islands developed.

After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse. Seeds were then harvested three to five months after transplanting. The method yielded single locus transformants at a rate of over 50% (Aldemita and Hodges1996, Chan et (Aldemita and Hodges (1996) Planta 199, 612-617; Chan et al. (1993) Plant Mol.Biol 22, 491-506; Hiei et al. (1994) Plant J. 6, 271-282).

Evaluation of the Transformed Rice Plants

Approximately 15 to 20 independent T0 transformants were generated. The primary transformants were transferred from tissue culture chambers to a greenhouse for growing and harvest of T1 seed. Five events of which the T1 progeny segregated 3:1 for presence/absence of the transgene were retained. For each of these events, 10 T1 seedlings containing the transgene (hetero- and homo-zygotes), and 5 T1 seedlings lacking the transgene (nullizygotes), were selected by PCR.

The selected T1 plants were transferred to a greenhouse. Each plant received a unique barcode label to link unambiguously the phenotyping data to the corresponding plant. The selected T1 plants were grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes were grown side-by-side at random positions. From the stage of sowing until the stage of maturity the plants were passed 10 times through a digital imaging cabinet. At each time point digital images (2048×1536 pixels, 16 million colors) were taken of each plant from at least 6 different angles. The parameters described below were derived in an automated way from the digital images using image analysis software.

Above Ground Plant Area

Plant area above ground area was determined by counting the total number of pixels from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground.

Plant Height

Plant height was determined by the distance between the horizontal lines going through the upper pot edge and the uppermost pixel corresponding to a plant part above ground. This value was averaged for the pictures taken on the same time point from the different angles and was converted, by calibration, to a physical distance expressed in mm. Experiments showed that plant height measured this way correlate with plant height measured manually with a ruler.

The mature primary panicles were harvested, bagged, barcode-labeled and then dried for three days in the oven at 37° C. The panicles were then threshed and all the seeds collected. The filled husks were separated from the empty ones using an air-blowing device. After separation, both seed lots were then counted using a commercially available counting machine. The empty husks were discarded. The filled husks were weighed on an analytical balance and the cross-sectional area of the seeds was measured using digital imaging. This procedure resulted in the set of seed-related parameters described below.

Number of Tillers;

The number of tillers was measured at the harvest by cutting the vegetative part and visually counting the number of tillers for each plant.

Total Seed Number Per Plant

The total seed number was measured by counting the number of filled husks harvested from a plant.

Total Seed Yield Per Plant

The total seed yield was measured by weighing all filled husks harvested from a plant.

TABLE E

| | Results from the evaluation of rice plants transformed with E2Fa | | |
|---|---|---|---|
| | Positive plants(1) | Negative plants(2) | p value(3) |
| number of tillers | 12.4 | 9.9 | p = 0.0005 |
| number of panicles | 8.1 | 6.3 | p = 0.0028 |

(1) Positive means positive for the visual marker and indicates that the constructs containing the visual marker gene and that the visual marker is expressed.
(2) Negative means negative for the visual marker and can be considered as "control" plants Positive and negative plants have been cultured and processed in the same way from seed to seed.
(3) The data on the number of tillers are analyzed with a Generalized Linear Model for a Poisson-distributed dependent variable ("Poisson regression model") with the transgenity as independent factor and event as blocking factor. A Chi-square test is performed on the deviance of this model for the factor transgenity. This test yields the probability level (p-value) of the null hypothesis (i.e. the number of tillers of transgene and non-transgene plants does not differ) being true. A p-value of 0.0005 indicates that the null hypothesis is extremely unlikely and therefore we can conclude with confidence that the transgenity has a real effect.)

The inventors surprisingly found that the E2F transformed plants showed more tillers, thus more branching, compared to the control plants not transformed with E2F. This means that they have an increased number of organs and therefore they show to have more biomass, thus increased yield. The effect of altering the number of organs could be explained by the altered expression and/or activity of the E2F in the meristem tissues, such as the meristem of the shoot. The effects of the transformation with pOleosin::E2Fa can occur very early during growth, probably affecting seed formation and embryo growth, for example influencing meristem functionality within the embryo leading to increased number of primordia and organs.

A link with the cotyledon phenotype of the 35S::E2Fa transformed plant, may be that there is 35S activity in the cotyledons which are consisting of tissues made before the formation of the shoot apical meristem (SAM) during development, but on the contrary, there is no 35S activity in the meristem. This means that the 35S promoter, although known to be a constitutive promoter, is not active in the SAM and that it is active in cotyledons where in combination with E2Fa it leads to modification of cell division in the cotyledons. In contrast, the Oleosin promoter, having a different expression pattern in the seed and/or embryo, may be highly expressed in the scutellum but also in the surrounding tissues such as the SAM, RAM. Therefore, in contrast to the 35S promoter, pOleosin is active later or within the SAM and affects more SAM, primordium and organ formation. So the phenotype observed in rice is probably correlated with the production of more cells within the SAM, leading to increased formation of primordia and consequently increased number of organs. Also, there the activity of the E2F in the inflorescence meristem may lead to increased flower and therefore also to increased seed number.

Positive plants also showed an increased number of panicles compared to control plants. This illustrates that the plants of the present invention have increased biomass and therefore increased yield. Furthermore the seeds from the panicles were analyzed and the inventors demonstrated that the plants transformed with E2F have increased seed yield (see FIG. 11). This effect can be explained by the presence of more seeds or by the increased seed size.

REFERENCES

Aldemita, R. R., and Hodges, T. K. (1996). Agrobacterium tumefaciens-mediated transformation of japonica and indica rice varieties. Planta 199, 612-617

Berger, F., Linstead, P., Dolan, L., and Haseloff, J. (1998). Stomata patterning on the hypocotyl of Arabidopsis thaliana is controlled by genes involved in the control of root epidermis patterning. Dev. Biol. 194, 226-234.

Britton, J. S., and Edgar, B. A. (1998). Environmental control of the cell cycle in Drosophila: nutrition activates mitotic and endoreplicative cells by distinct mechanisms. Development 125, 2149-2158.

Chaboute M. E., Clement B., and Philipps G. (2002) S phase and meristem-specific expression of the tobacco RNR1b gene is mediated by an E2F element located in the 5' leader. J Biol Chem; 277(20):17845-51

Chaboute, M. E., Clement, B., Sekine, M., Philipps, G., and Chaubet-Gigot, N. (2000). Cell cycle regulation of the tobacco ribonucleotide reductase small subunit gene is mediated by E2F-like elements. Plant Cell 12, 1987-1999.

Chan,M. T., Chang,H. H., Ho,S. L., Tong,W. F., and Yu,S. M. (1993). Agrobacterium-mediated production of transgenic rice plants expressing a chimeric alpha-amylase promoter/beta-glucuronidase gene. Plant Mol.Biol 22, 491-506.

Clough, S. J., and Bent, A. F. (1998). Floral dip: a simplified method for Agrobacterium-mediated transformation of Arabidopsis thaliana. Plant J. 16, 735-743.

Cockcroft, C. E., den Boer, B. G. W., Healy, J. M. S., and Murray, J. A. H. (2000). Cyclin D control of growth rate in plants. Nature 405, 575-579.

Creighton (1984) Proteins. W.H. Freeman and Company de Almeida Engler, J, de Groodt, R, Van Montagu, M, and Engler, G. (2001). In situ hybridization to mRMA of Arabidopsis tissue sections. Methods 23, 325-334.

De Veyider, L., Beemster, G. T. S., Beeckman, T., and Inzé, D. (2001). CKS1At overexpression in Arabidopsis thaliana inhibits growth by reducing meristem size and inhibiting cell-cycle progression. Plant J. 25, 617-626.

Doerner, P., Jorgensen, J. E., You, R., Steppuhn, J., and Lamb, C. (1996). Control of root growth and development by cyclin expression. Nature 380, 520-523.

Edgar, B. A., and Orr-Weaver, T. L. (2001). Endoreplication cell cycles: more for less. Cell 105, 297-306.

Galbraith, D. W., Harkins, K. R., and Knapp, S. (1991). Systemic endopolyploidy in Arabidopsis thaliana. Plant Physiol. 96, 985-989.

Gendreau ,E., Traas, J., Desnos, T., Grandjean, O., Caboche, M., and Hofte,H. (1997). Cellular basis of hypocotyl growth in Arabidopsis thaliana. Plant Physiol. 114, 295-305.

Gerdes, H. H., and Kaether, C. (1996). Green fluorescent protein: applications in cell biology. FEBS Lett. 389, 44-47.

Giacomin, L. T., and Szalay, A. A. (1996). Expression of a PAL1 promoter luciferase gene fusion in Arabidopsis thaliana in response to infection by phytopathogenic bacteria. PI. Sci. 116 (1), 59-72

Grafi, G., Burnett,R. J., Helentjaris, T., Larkins, B. A., DeCaprio, J. A., Sellers, W. R., and Kaelin, W. G., Jr. (1996). A maize cDNA encoding a member of the retinoblastoma protein family: involvement in endoreduplication. Proc. Natl. Acad. Sci. USA 93, 8962-8967.

Grafi, G., and Larkins, B. A. (1995). Endoreduplication in maize endosperm: involvement of M phase-promoting factor inhibition and induction of S phase-related kinases. Science 269, 1262-1264.

Guy, C. T., Zhou, W., Kaufman, S., and Robinson, M. 0. (1996). E2F-1 blocks terminal differentiation and causes proliferation in transgenic megakaryocytes. Mol. Cell. Biol. 16, 685-693.

Hartman,S. C., and Mulligan,R. C., (1988). Two dominant-acting selectable markers for gene transfer studies in mammalian cells Proc. NatI. Acad. Sci. USA 85, 8047-8051

Helin, K. (1998). Regulation of cell proliferation by the E2F transcription factors. Curr. Opin. Gent. Dev. 8, 28-35.

Hemerly, A., de Almeida Engler, J., Bergounioux, C., Van Montagu, M., Engler, G., Inzé, D., and Ferreira, P. (1995). Dominant negative mutants of the Cdc2 kinase uncouple cell division from iterative plant development. EMBO J. 14, 3925-3936.

Herrera-Estrella, L., De Block, M., Messens, E., Hernalsteens, J.-P., Van Montagu, M., and Schell,J. (1983). Chimeric genes as dominant selectable markers in plant cells EMBO J. 2, 987-995

Hiei, Y., Ohta, S., Komari, T., and Kumashiro, T. (1994). Efficient transformation of rice (Oryza sativa L.) mediated by Agrobacterium and sequence analysis of the boundaries of the T-DNA. Plant J. 6, 271-282.

Huntley, R., Healy, S., Freeman, D., Lavender, P., de Jager, S., Greenwood, J., Makker, J., Walker, E., Jackman, M., Xie, Q., Bannister, A. J., Kouzarides, T., Gutierrez, C., Doonan, J. H., and Murray, J. A. (1998). The maize retinoblastoma protein homologue ZmRb-1 is regulated during leaf development and displays conserved interactions with G1/S regulators and plant cyclin D (CycD) proteins. Plant Mol. Biol. 37, 155-169.

Huntley, R. P., and Murray, J. A. H. (1999). The plant cell cycle. Current Opinion in Plant Biology 2, 440-446.

Jefferson, R. A., Kavanagh, T. A. and Bevan, B. W. (1987). GUS fusions: beta-glucuronidase as a sensitive and versatile gene fusion marker in higher plants. EMBO J. 6 3901-3907

Koncz, C., and Schell, J. (1986). The promoter of TL-DNA gene 5 controls the tissue¤specific expression of chimaeric genes carried by a novel type of Agrobacterium binary vector. Mol. Gen. Genet. 204, 383-396.

Leone, G., DeGregori, J., Yan, Z., Jakoi, L., Ishida, S., Williams, R. S., and Nevins, J. R. (1998). E2F3 activity is regulated during the cell cycle and is required for the induction of S phase. Genes Dev. 12, 2120-2130.

Magyar, Z., Atanassova, A., De Veylder, L., Rombauts, S., and Inze, D. (2000). Characterization of two distinct DP-related genes from Arabidopsis thaliana. FEBS Lett. 486, 79-87.

Marsh, J. L., Erfle,M. and E. J. Wykes (1984). The plC plasmid and phage vectors with versatile cloning sites for recombinant selection by insertional inactivation. Gene 32: 481-485.

McConlogue, 1987, In: Current Communications in Molecular Biology, Cold Spring Harbor Laboratory ed Meijer, M., and Murray, J. A. H. (2001). Cell cycle controls and the development of plant form. Current Opinion in plant Biology 4, 44-49.

Melaragno, J. E., Mehrotra, B., and Coleman, A. W. (1993). Relationship between endopolyploidy and cell size in epidermal tissue of Arabidopsis. Plant Cell 5, 1661-1668.

Mironov, V., De Veylder, L., Van Montagu, M., and Inze, D. (1999). Cyclin-dependent kinases and cell division in plants- the nexus. Plant Cell 11, 509-522.

Müller, H., and Helin, K. (2000). The E2F transcription factors: key regulators of cell proliferation. Biochim. Biophys. Acta 1470, M1-M12.

Murray, E. E., Lotzer, J., and Eberle, M. (1989). Codon usage in plant genes. Nucleic Acids Res. 17, 477-498.

Paszkowski (ed.), Homologous Recombination and Gene Silencing in Plants. Kluwer Academic Publishers (1994).

Peralta, E. G., Hellmiss, R., and Ream, W. (1986). Overdrive, a T-DNA transmission enhancer on the A. tumefaciens tumour-inducing plasmid. EMBO J. 5, 1137-1142.

Ramirez-Parra, E., and Gutierrez, C. (2000). Characterization of wheat DP, a heterodimerization partner of the plant E2F transcription factor which stimulates E2F-DNA binding. FEBS Lett. 486, 73-78.

Ramirez-Parra, E., Xie, Q., Boniotti, M.B. & Gutierrez, C. (1999). The cloning of plant E2F, a retinoblastoma-binding protein, reveals unique and conserved features with animal Gl/S regulators. Nucleic Acids Res. 27, 3527-3533.

Raz, V., and Koornneef, M. (2001). Cell division activity during apical hook development. Plant Physiol. 125, 219-226.

Reiss, C. Experiments in Plant Physiology, Prentice Hall, Upper Saddle River, N.J., (1994)

Sambrook, Molecular Cloning; A Laboratory Manual, 2nd Edition, Cold Spring Harbor Laboratory Press, Cold Spring Harbor, N.Y. (1989)

Srikantha, T., Klapach, A., Lorenz, W. W., Tsai, L. K., Laughlin, L. A., Gorman, J. A., and Soll, D. R. (1996). The sea pansy Renilla reniformis luciferase serves as a sensitive bioluminescent reporter for differential gene expression in Candida albicans. J. Bact. 178, 121-129

Seifter,S. and Englard,S (1990). Analysis for protein modifications and nonprotein cofactors. Meth. Enzymol. 182: 626-646

Sekine, M., Ito, M., Uemukai, K., Maeda, Y., Nakagami, H., and Shinmyo, A. (1999). Isolation and characterization of the E2F-like gene in plants. FEBS Lett. 460, 117-122.

Stevens R., Mariconti L., Rossignol P., Perennes C., Cella R., and Bergounioux C., (2002 Jun. 27 internet publication) Two E2F sites in the Arabidopsis MCM3 promoter have different roles in cell cycle activation and meristematic expression, J Biol Chem.

Tamura, K., Kimura, M., and Yamaguchi, I. (1995). Blasticidin S deaminase gene (BSD): a new selection marker gene for transformation of Arabidopsis thaliana and Nicotiana tabacum Biosci. Biotechnol. Biochem. 59 (12), 2336-2338

Thompson, J. D., Higgins, D. G., and Gibson,T.J., (1994). CLUSTAL W: improving the sensitivity of progressive multiple sequence alignment through sequence weighting, position-specific gap penalties and weight matrix choice. Nucleic Acids Res. 22 (22), 4673 - 4680

Tijssen, Laboratory Techniques in Biochemistry and Molecular Biology-Hybridization with Nucleic Acid Probes, Part I, Chapter 2 'Overview of principles of hybridization and the strategy of nucleic acid probe assays', Elsevier, New York (1993)

Valvekens, D., Van Montagu, M., and Van Lijsebeltens, M. (1988). Agrobacterium tumefaciens-mediated transformation of Arabidopsis thaliana root explants by using kanamycin selection. Proc. NatI. Acad. Sci. USA 85, 5536__5540.

van Engelen, F. A. et al. (1995). pBINPLUS: an improved plant transformation vector based on pBIN19. Transgenic Res. 4, 288-290.

van Haaren, M. J., Sedee, N. J., Schilperoort, R. A., and Hooykaas, P. J. (1987). Overdrive is a T-region transfer enhancer which stimulates T-strand production in Agrobacterium tumefaciens. Nucleic Acids Res. 15, 8983-8997.

Wang, J., Helin, K., Jin, P. & Nadal_Ginard, B. (1995). Inhibition of in vitro myogenic differentiation by cellular transcription factor E2F1. Cell Growth Differ. 6, 1299-1306.

Weinberg, R. A. (1995). The retinoblastoma protein and cell cycle control. Cell 81, 323-330.

Wold F., Posltranslational Protein Modifications: Perspectives and Prospects, pp. 1-12 in Posttranslational Covalent Modification of Proteins, B.C. Johnson, Ed., Academic Press, New York (1983))

The invention claimed is:

1. A method for the production of a transgenic plant having increased biomass or yield, said method comprising:

(a) providing a DNA construct comprising a gene encoding an E2F transcription factor having the amino acid sequence of SEQ ID NO:20 or SEQ ID NO:2, operably linked to a seed-specific promoter;

(b) transforming said DNA construct of (a) into a plant cell;

(c) cultivating the transgenic cell obtained from step (b) under conditions promoting regeneration and mature plant growth; and (d) selecting and evaluating said plant of (c) during the course of development to registrate its phenotypic or morphological characteristics, wherein said phenotypic or morphological characteristics are increased biomass or yield.

2. The method of claim 1 wherein said increased biomass or yield comprises an increase in organ number or an increase in organ size.

3. The method of claim 2 wherein said organ is at least one of a flower, leaf, stem, seed, root, tiller or tuber.

4. The method of claim 1 wherein the increased biomass or yield comprises an increase in tiller, panicle, branch or ear number.

5. The method of any one of claims 1-4 wherein said increased biomass or yield comprises increased seed yield.

* * * * *